US006818360B1

(12) United States Patent
Phan et al.

(10) Patent No.: US 6,818,360 B1
(45) Date of Patent: Nov. 16, 2004

(54) QUARTZ MASK CRACK MONITOR SYSTEM FOR RETICLE BY ACOUSTIC AND/OR LASER SCATTEROMETRY

(75) Inventors: Khoi A. Phan, San Jose, CA (US); Bhanwar Singh, Morgan Hill, CA (US); Bharath Rangarajan, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 250 days.

(21) Appl. No.: 10/261,571

(22) Filed: Sep. 30, 2002

(51) Int. Cl.[7] .......................... G03F 9/00; G01N 21/88
(52) U.S. Cl. ...................... 430/5; 430/30; 356/237.1; 356/237.5; 382/144; 382/149
(58) Field of Search ..................... 430/5, 30; 356/237.1, 356/237.2, 237.3, 237.4, 237.5, 237.6; 382/144, 149

(56) References Cited

U.S. PATENT DOCUMENTS 6,665,065 B1 * 12/2003 Phan et al. ............... 356/237.1

6,674,522 B2 * 1/2004 Krantz et al. ............ 356/237.1

* cited by examiner

*Primary Examiner*—Christopher G. Young
(74) *Attorney, Agent, or Firm*—Amin & Turocy, LLP

(57) ABSTRACT

A system that monitors and controls a phase shift mask fabrication process is disclosed. Acoustic beams and/or beams of light are selectively directed at portions of the mask to scan the mask as it matriculates through the fabrication process. Portions of the beams that pass through and/or are reflected from the mask are collected and examined, such as in accordance with scatterometry based techniques, to determine, for example, whether cracks or other defects are forming on or within the mask, and/or whether features, such as apertures, are being formed as desired. The measurements can be employed to generate feed forward and/or feedback control data that can utilized to selectively adjust one or more fabrication components and/or operating parameters associated therewith to adapt the fabrication process. Controlling the mask fabrication process facilitates improved mask fabrication and resulting chip quality as compared to conventional systems.

24 Claims, 19 Drawing Sheets

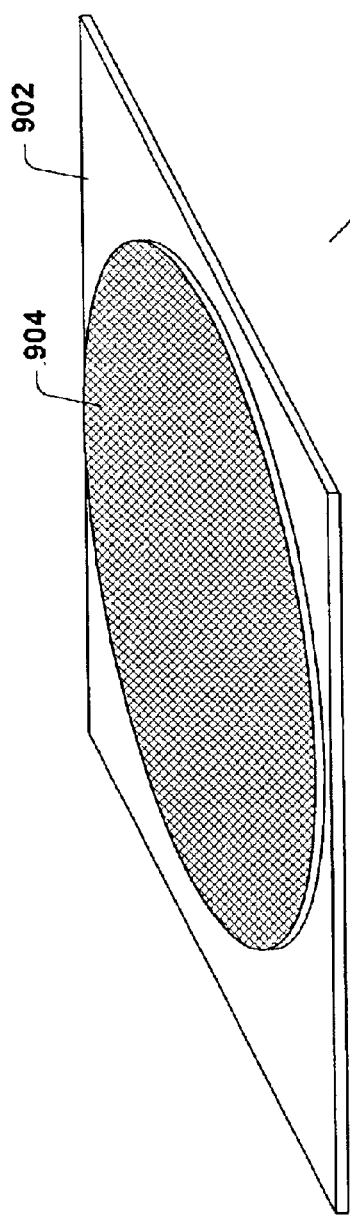
FIG. 9
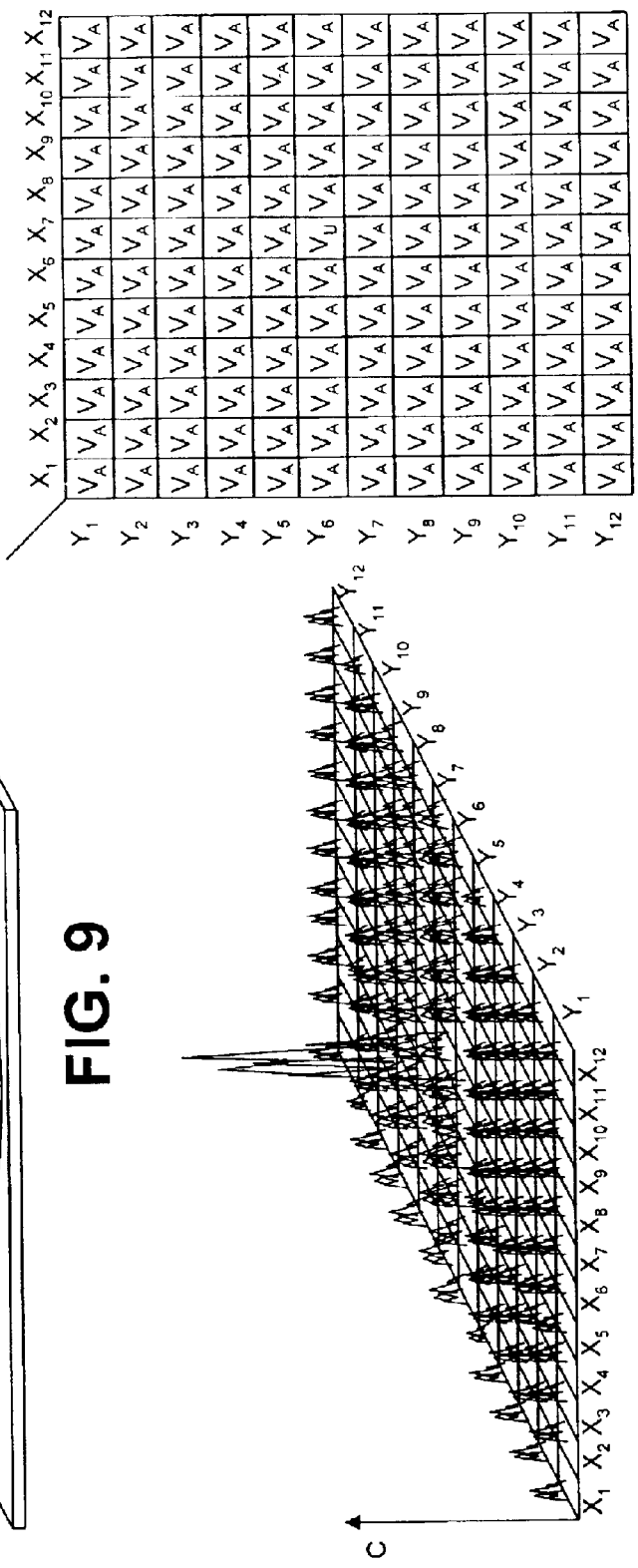
FIG. 11
FIG. 10

QUARTZ MASK CRACK MONITOR SYSTEM FOR RETICLE BY ACOUSTIC AND/OR LASER SCATTEROMETRY

TECHNICAL FIELD

The present invention generally relates to semiconductor processing, and in particular to a system and methodology for monitoring and/or controlling the fabrication of a phase shift mask.

BACKGROUND

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required in integrated circuits (ICs) fabricated on small rectangular portions of the wafer, commonly known as dies. This may include the width and spacing of interconnecting lines, spacing and diameter of contact holes, the surface geometry such as corners and edges of various features as well as the surface geometry of other features. To scale down device dimensions, more precise control of fabrication processes are required. The dimensions of and between features can be referred to as critical dimensions (CDs). Reducing CDs, and reproducing more accurate CDs facilitates achieving higher device densities through scaled down device dimensions and increased packing densities.

The process of manufacturing semiconductors or ICs typically includes numerous steps (e.g., exposing, baking, developing), during which hundreds of copies of an integrated circuit may be formed on a single wafer, and more particularly on each die of a wafer. In many of these steps, material is overlayed or removed from existing layers at specific locations to form desired elements of the integrated circuit. Generally, the manufacturing process involves creating several patterned layers on and into a substrate that ultimately forms the complete integrated circuit. This layering process creates electrically active regions in and on the semiconductor wafer surface. The layer to layer alignment and isolation of such electrically active regions depends, at least in part, on the precision with which features can be placed on a wafer. If the layers are not aligned properly, overlay errors can occur compromising critical dimensions and the performance of the electrically active regions and adversely affecting chip quality and reliability.

The requirement of small features with close spacing between adjacent features requires the implementation of high-resolution lithographic processes. In general, lithography refers to processes for pattern transfer between various media. It is a technique used for integrated circuit fabrication in which a silicon slice, the wafer, is coated uniformly with a radiation-sensitive film, the photoresist, and an exposing source (such as light, x-rays, or an electron beam) illuminates selected areas of the surface of the film through an intervening master template, mask or reticle for a particular pattern. The lithographic coating is generally a radiation-sensitized coating suitable for receiving a projected image of the subject pattern. Once the image is projected, it is indelibly formed in the photoresist coating.

Light projected onto the photoresist changes properties (e.g. solubility) of the coating such that different portions thereof (e.g. the illuminated or un-illuminated portions, depending upon the type of photoresist) can be manipulated in subsequent processing steps. For example, regions of a negative photoresist become insoluble when illuminated by an exposure source such that the application of a solvent to the photoresist during a subsequent development stage removes only non-illuminated regions of the photoresist. The pattern formed in the negative photoresist layer is, thus, the negative of the pattern defined by opaque regions of the template. By contrast, in a positive photoresist, illuminated regions of the photoresist become soluble and are removed via application of a solvent during development. The pattern formed in the positive photoresist is, thus, a positive image of opaque regions on the template. Less soluble portions of the photoresist are removed in subsequent processing stages after the image has been transferred onto the wafer. The accuracy with which patterns are transferred onto the wafer is thus important to the success of the semiconductor fabrication process.

As feature sized are continually reduced, however, limitations due to the wavelength of the light utilized in semiconductor processing can adversely affect the accuracy of pattern transfers. More particularly, as feature sizes approach the wavelength of the light utilized in processing, diffraction can occur. Diffraction is a property of wave motion, in which waves spread and bend when passed through small apertures or around barriers. The pattern(s) defined within masks can contain many such small apertures and barriers, and the bending and/or spreading of the light waves is more pronounced when the size of the aperture or the barrier approximates or is smaller than the wavelength of the incoming wave. Diffraction can occur for instance where light passes adjacent an edge of a pattern formed in the mask and is scattered in multiple directions by the edge. Diffraction can lead, for example, to rounded features and/or features that do not have a desired size and/or shape. Diffraction can also result in a reduction in intensity where exposure is desired and an increase in intensity in areas where no exposure is desired.

For example, in prior art FIG. 20, a light source is directing light waves 2002 at a mask 2004. Some of the light waves 2002 pass through an aperture 2006 that is close to the size of the wavelength of the light waves 2002. The mask 2004 has been designed to develop a region 2008 on a photo resist layer 2010, so that two desired features 2012 and 2014 can be formed. The features 2012 and 2014 are desired to be rectangular, with substantially square edges. The aperture 2006 is small because the desired features 2012 and 2014 are correspondingly small.

With conventional lithography, the light waves 2002 may pass directly through the aperture 2006, exposing the region 2008, but the light waves 2002 may also be diffracted as illustrated by light waves 2016, 2018 and 2020. The diffracted wave 2016 has exposed a region 2022 and the diffracted wave 2018 has exposed a region 2024. Neither region 2022 nor region 2024 were intended to be exposed. Further, diffracted wave 2020 has exposed a triangular area 2026 on either side of the region 2008. Thus the desired feature 2014 may not have a substantially square edge due to the undesired region 2026 being exposed by the diffracted wave 2020.

Reticles known as phase shift masks can be utilized in photolithographic processing to account for diffraction. Phase shift masks facilitate compensating for the effects of diffraction which limit the precision and size to which imaged features can be reduced. The underlying concept of a phase shift mask is to selectively introduce interference and cancellation of light at portions of an image where diffraction effects may deteriorate the resolution of the image.

In lithography, resolution is typically defined as the smallest distance two features can be spaced apart while removing all photo resist between the features, and is equal to:

$$D = k1 * (lambda/NA)$$

where d is the resolution, lambda is the wavelength of the exposing radiation, NA is the numerical aperture of the lens, and k1 is a process dependent constant typically having a value of approximately 0.5. While resolution may be improved by decreasing the wavelength or by using a lens with a larger NA, decreasing the wavelength and increasing the numerical aperture decreases the depth of focus (since depth of focus is proportional to lambda/NA$^2$). In phase shift masks, features are surrounded by light transmitting regions that shift the phase of transmitted light. Masks may be constructed to shift the phase of transmitted light by varying amounts, such as 30 degrees, 60 degrees, 90 degrees, and 180 degrees. In this way, diffracted light can be effectively cancelled, resulting in a better image transfer and improved quality chips.

SUMMARY OF THE INVENTION

The following presents a simplified summary of the invention in order to provide a basic understanding of some aspects of the invention. This summary is not an extensive overview of the invention. It is intended to neither identify key cr critical elements of the invention nor delineate the scope of the invention. Its purpose is merely to present some concepts of the invention in a simplified form as a prelude to the more detailed description that is presented later.

The present invention provides a system that facilitates monitoring and/or controlling a phase shift mask fabrication process. One or more acoustic and/or light (e.g., laser) beams arc selectively directed at a mask matriculating through the fabrication process to facilitate scanning portions of the mask to detect defects, such as, for example, cracks in a quartz layer. Some of the beams pass through the mask, while other beams are reflected from the mask. Beams that are reflected from the mask can be examined to reveal information about the surface of the mask, while beams passing through the mask, such as acoustic waves, can be utilized to expose, for example, defects or other features formed below the surface of the mask.

Cracks or fractures may develop in masks, for instance, during an etching stage of the phase shift mask fabrication process and can impinge on resulting chip quality as the defect may be propagated onto the wafer during image transfer and/or may interfere with phase shifting to mitigate the adverse affects of diffraction. Controlling the mask fabrication process, such as with runtime feedback, facilitates improved mask fabrication as compared to conventional systems and thus facilitates achieving smaller feature sizes via more precise control of phase shifting of light passing through the phase shift mask.

By way of example, one or more etching components may be employed in fabricating a phase shift mask. The etching process can be monitored by comparing signatures generated from beams reflected from and/or that pass through the mask to desired signatures. By comparing desired signatures to measured signatures, runtime feedback may be employed to control the etching component and/or one or more operating parameters associated therewith, such as to adapt the etching process. For example, at the first sign(s) of a fracture, the concentration of etchants applied to the mask can be adjusted to halt and/or rectify the formation of the defect. As a result, more desirable etching can be achieved, which can in turn increase fidelity of image transfer since more precise phase shifting and the resulting interference and cancellation may thereby be facilitated.

To the accomplishment of the foregoing and related ends, certain illustrative aspects of the invention are described herein in connection with the following description and the annexed drawings. These aspects are indicative, however, of but a few of the various ways in which one or more of the principles of the invention may be employed and the present invention is intended to include all such aspects and their equivalents. Other advantages and novel features of the invention will become apparent from the following detailed description of the invention when considered in conjunction with the drawings.

BRIEF DESCRIPTION OF THE DRAWINGS

The present invention is illustrated by way of example in the accompanying figures.

FIG. 9 illustrates a perspective view of a grid mapped mask according to one or more aspects of the present invention.

FIG. 10 illustrates plots of measurements taken at grid mapped locations on a mask in accordance with one or more aspects of the present invention.

FIG. 11 illustrates a table containing entries corresponding to measurements taken at respective grid mapped locations on a mask in accordance with one or more aspects of the present invention.

DETAILED DESCRIPTION

Figure 1:
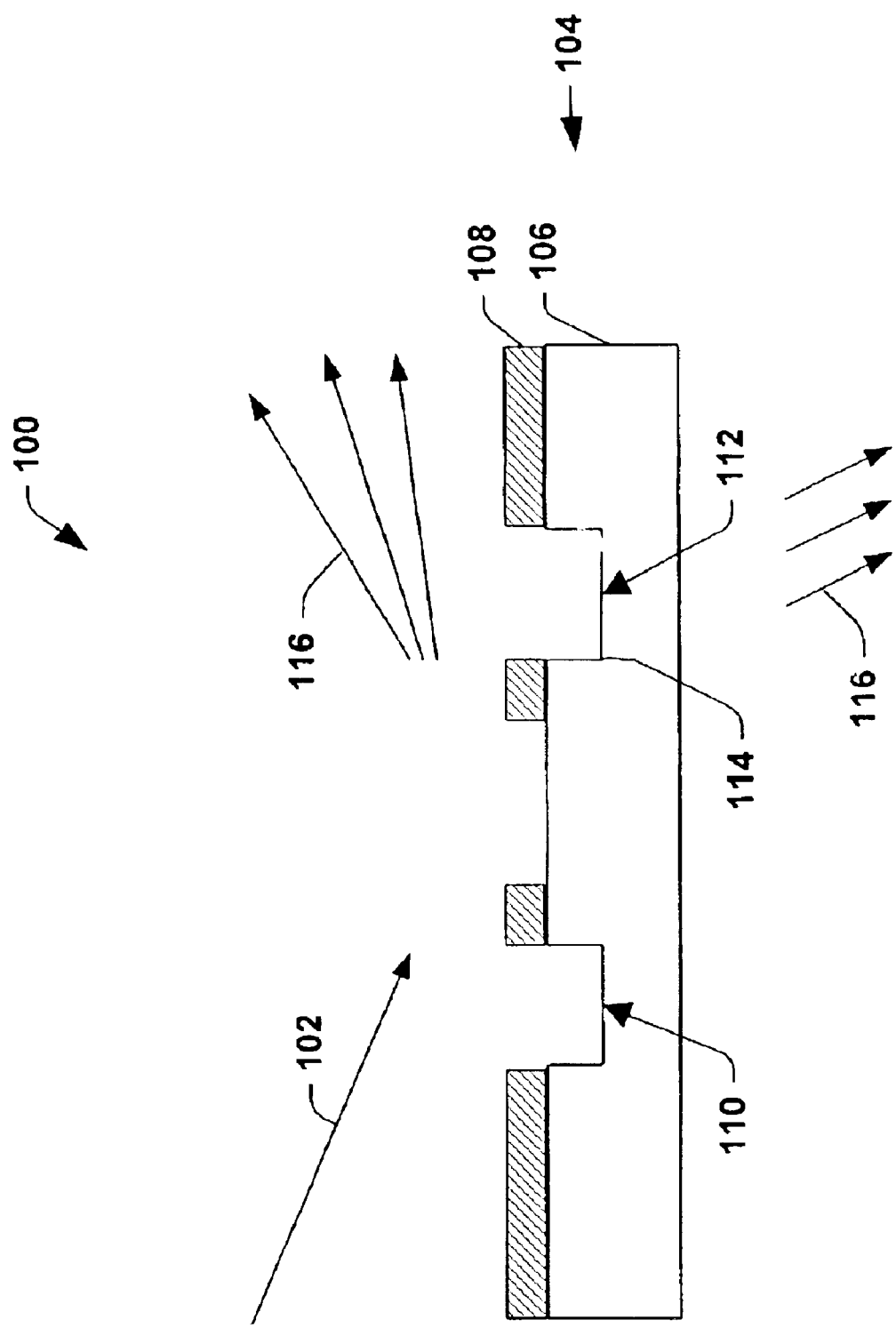
FIG. 1 illustrates a beam being directed at a phase shift mask, in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that one or more aspects of the present invention may be practiced with a lesser degree of these specific details. In other instances, known structures and devices may be shown in block diagram form in order to facilitate describing one or more aspects of the present invention.

The term "component" as used herein includes computer-related entities, either hardware, a combination of hardware and software, software, or software in execution. For example, a component may be a process running on a processor, a processor, an object, an executable, a thread of execution, a program and a computer. By way of illustration, both an application running on a server and the server can be components. By way of further illustration, both a stepper and a process controlling the stepper can be components.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

FIG. 1 illustrates a system 100 for monitoring and/or controlling phase shift mask (PSM) fabrication. In the system 100, one or more beams 102 are selectively directed at a phase shift mask 104 to scan across the mask throughout the fabrication process. The beams can be, for example, acoustic and/or ultrasonic waves and/or light generated from a source such as a laser. The beams can be partially and/or entirely reflected by and/or pass through the mask and are affected (e.g., refracted, diffracted, altered in magnitude) by the properties (e.g., defects) of the mask. Portions of the beams that are reflected from the mask generally reveal information about the surface of the mask, while portions of the beams that pass through the mask, such as acoustic waves, can be utilized to expose defects below the surface of the mask. The mask 104 is illustrated as including a substantially transparent layer 106 (e.g., quartz) and a substantially opaque layer 108 (e.g., chrome) lying over the transparent layer 106. While the mask 104 is illustrated as including two layers, it is to be appreciated that the phase shift mask can have a different number of layers. Furthermore, while the substantially transparent layer 106 may be quartz, it is to be appreciated that other substantially transparent layers may be employed in accordance with the present invention. Further still, while the substantially opaque layer 108 may be chrome, it is to be appreciated that other substantially opaque layers may be employed in accordance with aspects of the present invention.

The mask 104 is illustrated as having two apertures 110, 112 processed (e.g., etched) therein. According to one or more aspects of the present invention, the system 100 can detect fine cracks 114 or fractures that may develop in the mask, either on or below a surface region of the mask. Such defects can occur during an etching stage of the fabrication process, for example. It will be appreciated, however, that other defects and/or processing parameters can also be measured, such as pinholes, air bubbles, structural irregularities, the depth of apertures, the width of apertures, the slope of apertures, etc. The system 100 can thus be employed to improve phase shift mask quality, and thus the quality of patterns projected during semiconductor fabrication processes. It will be appreciated that the system 100 can be employed in-situ (e.g., during fabrication) to control the fabrication of the mask 104 and/or can be employed ex-situ, (e.g., post fabrication) in processes like quality control.

The system 100 operates, at least in part, by directing the beam 102 at the mask 104 and then collecting and analyzing differences in the beam after it interacts with the mask 104 and is reflected, refracted, diffracted and/or passes through 116 the mask. Defects such as cracks 114 in the mask will affect the beam altering its phase and/or intensity reinforcing it in certain directions and diminishing it in other directions, thus providing for the creation of unique signatures for different wavelengths and/or angles of incidence of the beam directed onto the mask. The altered beam 116 is thus indicative of at least one parameter of the mask fabrication process (e.g., cracks, fractures, impurities, bubbles, aperture depth, aperture width, wall slope). The parameters are important to the fidelity of the pattern transfer process due to effects on phase shifting and diffraction, and thus monitoring for cracks, other defects, the depth, width and/or trench wall slopes in the masks facilitates fabricating higher quality phase shift masks as compared to conventional systems.

It is to be appreciated that the process of fabricating phase shift masks may include many steps, of which etching is merely one step that may be repeated any number of times. For instance, another step in fabricating phase shift masks is depositing a chrome layer on a clean substrate layer. Once deposited, openings (apertures) are processed (e.g., etched) into the chrome layer. Watching for fractures in the mask facilitates controlling the process to mitigate the progression of such defects, such as by regulating the rate at which apertures are processed (e.g., etched) into the chrome layer and substrate (e.g., quartz, $SiO_2$), such as by controlling the volume, concentration and rate of etchants applied to the mask.

It will be appreciated that light transmitted through phase shift masks described with respect to aspects of the present invention will be phase shifted. More particularly, light transmitted through substantially transparent regions on either side of patterned opaque features will be phase-shifted (e.g., 0 degrees, 60 degrees, 120 degrees, 180 degrees). Diffracted light below the opaque regions is cancelled by the phase-shifted light to create null areas. Cracks or fractures in the mask can affect the precision with which such areas can be created and can thus adversely affect the functioning of the phase shift masks.

It will be further appreciated that phase shift masks depend on interference of ordered light. Light can be modeled as waves propagating through space, where the waves have a wavelength and an intensity. Wavelength is related to the color of the light and intensity is related to the brightness of the light. Incoherent light, (e.g., normal everyday light), includes waves of various lengths and intensities, traveling in different directions. Coherent light (e.g., laser light) can be produced so that the waves share a common wavelength, a common intensity and have their peaks in phase. Interference, both constructive and destructive, can be employed with coherent light in a PSM. However, the constructive and destructive effects depend, at least in part, on the presence of defects, such as cracks or fractures in the mask, which can impede the desired interference, and thus reduce the quality of the pattern transferred to a wafer.

The wavelengths that can be employed with a PSM depend, at least in part, on the depth to which an aperture in the mask is etched. Etching depths in a PSM can, for example, be modeled by:

$$\Delta\phi=2\pi d(n-1)/\lambda,$$

where $\Delta\phi$ is the phase shift, d is the depth difference between shifted and unshifted spaces, n is the index of refraction, and $\lambda$ is the wavelength. Thus, the phase shift depends, at least in part, on the depth difference between shifted and unshifted spaces. Defects such as cracks or fractures can affect the uniformity of aperture depth and thus monitoring for cracks which can affect depths can, for example, facilitate better pattern transfer and improved chip quality.

Figure 21:
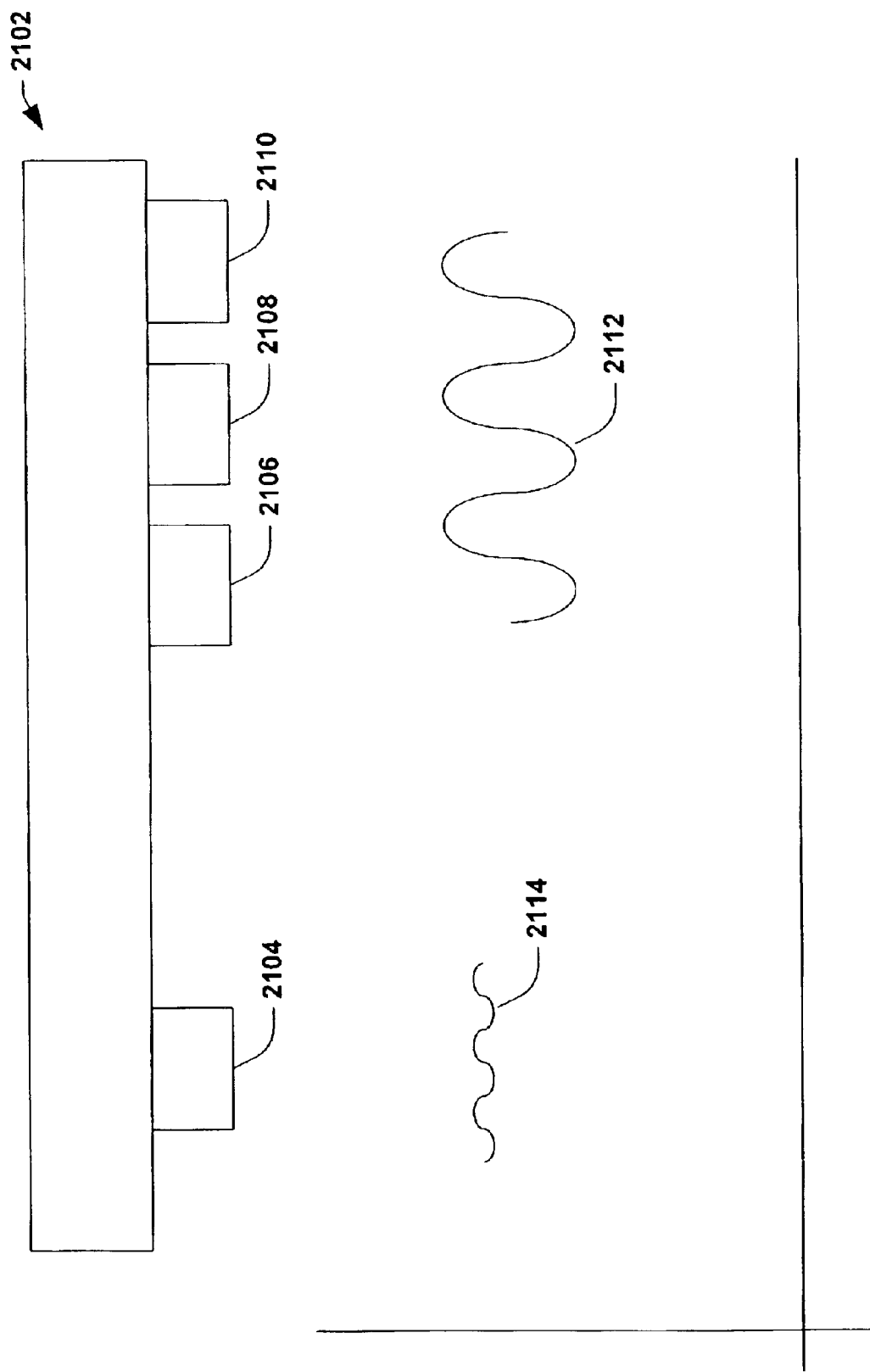
FIG. 21 illustrates an aerial intensity plot of isolated and periodic structures on a mask or reticle.

It will be still further appreciated that the resolution of lithographic processes may be better for periodic features, such as those found in memory devices (e.g. DRAMs) since a greater percentage of the exposing radiation is contained in diffraction nodes of the periodic structures compared to that contained in the diffraction nodes of isolated features. For example, prior art FIG. 21 illustrates an aerial plot of intensity under a mask 2102 having an isolated feature 2104 and periodic features 2106, 2108, and 2110 having a dimension near the resolution limit of the process. The contrast (difference in intensity) between masked and unmasked regions is much greater for the periodic features 2106, 2108 and 2110 (curve 2112) than for the isolated feature 2104 (curve 2114). Thus, for a given combination of exposing conditions, at some dimension, isolated feature 2104 cannot be resolved simultaneously with the periodic features 2106, 2108 and 2110 that are within the resolution limit of the process.

Figure 2:
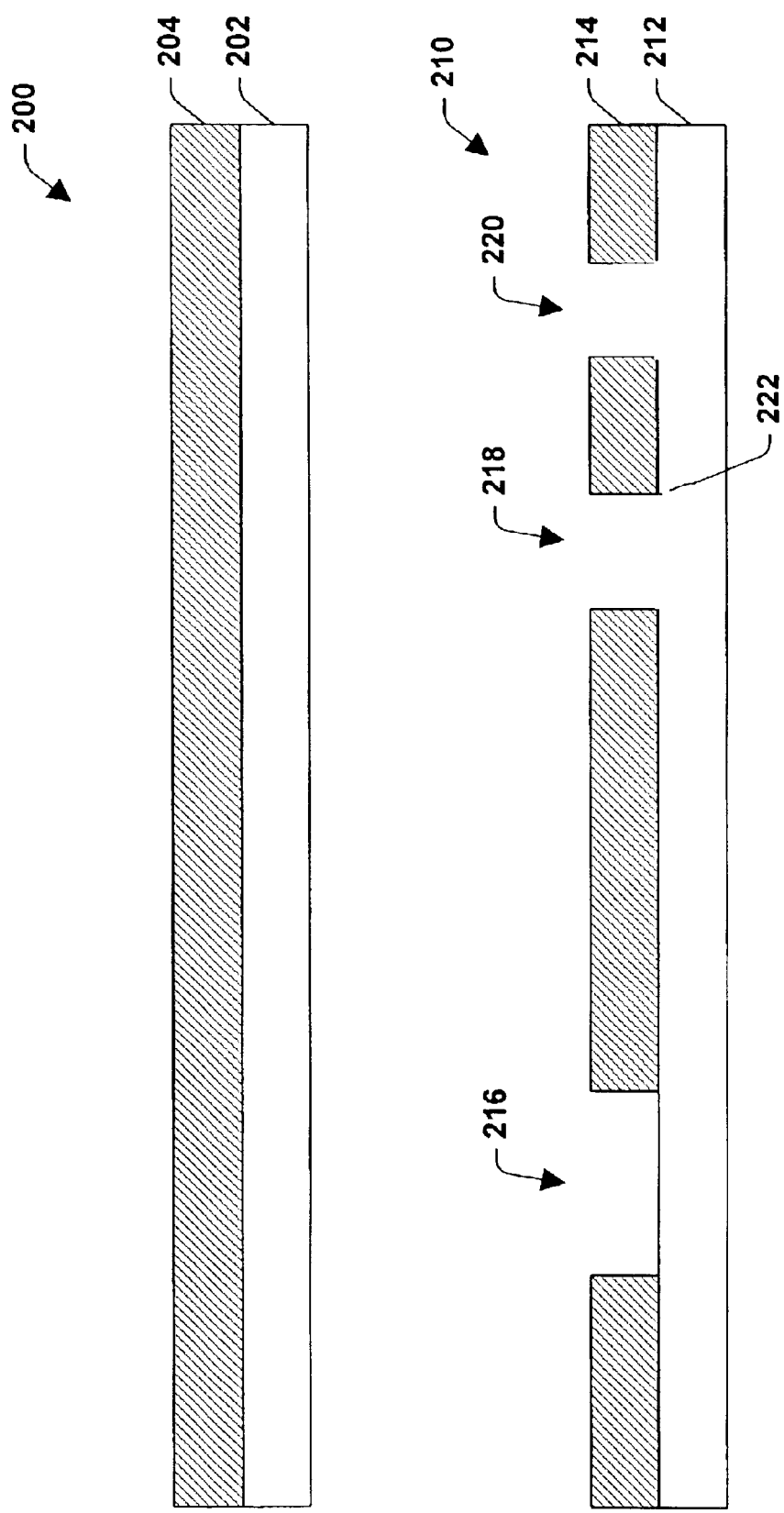
FIG. 2 illustrates light beams being directed at a patterned and an un-patterned phase shift mask.
Figure 3:
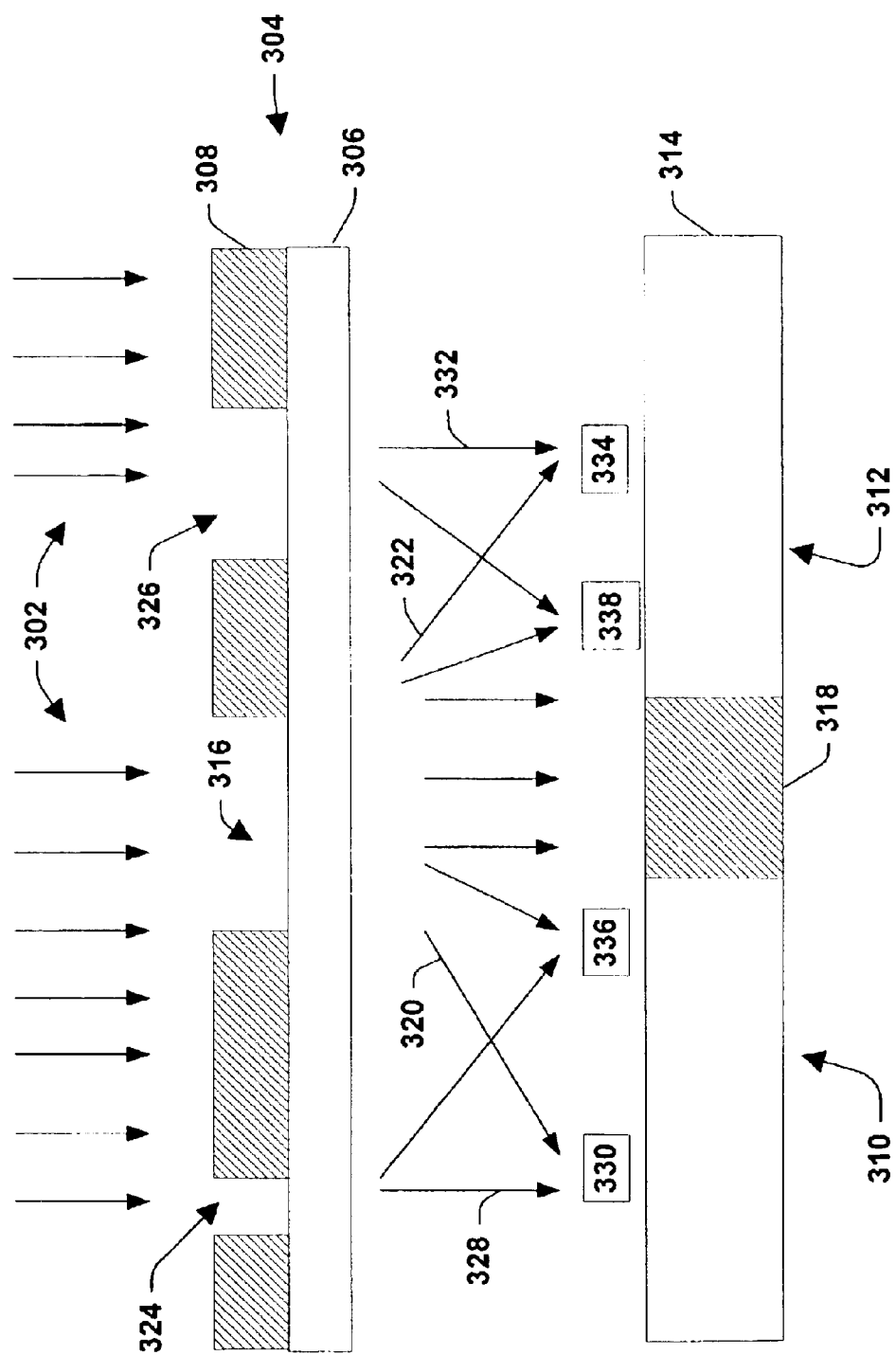
FIG. 3 illustrates a phase shift mask with light passing there-through and canceling diffracted light.
Figure 4:
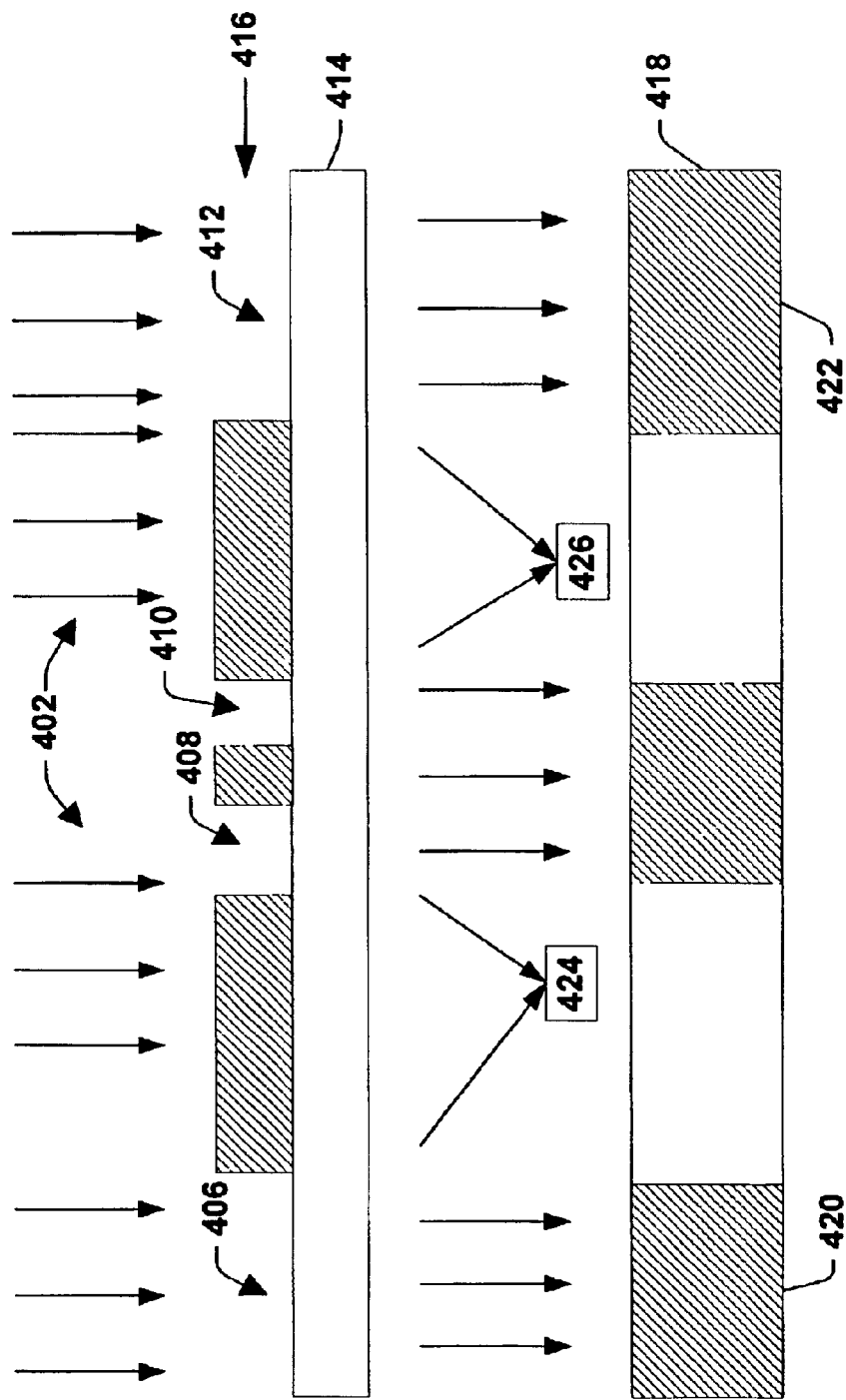
FIG. 4 illustrates another phase shift mask with light passing there-through to cancel diffracted light.

FIGS. 2–4 illustrate examples of phase shift masks and briefly illustrate the operation of diffraction and cancellation in phase shift masks, such as are discussed with respect to aspects of the present invention. One theory explaining diffraction is that each point of a wave on a flat wave front may be a source of secondary, spherical wavelets. Before reaching a barrier or aperture, the secondary wavelets may add to the original wave front. When the wave front approaches an aperture or barrier, the wavelets approaching the unobstructed region pass through the barrier, while other wavelets do not pass. When the size of the aperture approaches the wavelength of or is smaller than the wavelength of the incoming wave, only a few wavelets may pass through the aperture. The wavelets that pass through the aperture or around the barrier may then be a source of more wavelets that expand in all directions from the point of the obstruction, and the shape of the new wave front is curved. The wavelets of these diffracted, or bent, waves can now travel different paths and subsequently interfere with each other, producing interference patterns. The shape of these patterns depends on the wavelength and the size of the aperture or barrier. Diffraction can be thought of as the interference of a large number of coherent wave sources, and thus, diffraction and interference are substantially similar phenomena.

Turning to FIG. 2, a phase shift mask 200 is illustrated. The mask includes a quartz layer 202, through which light waves may pass, and an opaque chrome layer 204, through which light waves may not pass. There are no apertures etched into the mask 200. FIG. 2 also illustrates a processed phase shift mask 210 which similarly includes a quartz layer 212, through which light waves may pass, and an opaque chrome layer 214, through which light waves may not pass. But the processed phase shift mask 210 also includes three apertures 216, 218 and 220, through which light may pass. The aperture 216 was fabricated by etching away substantially all of the chrome layer 214 at the location of the aperture 216. But practically none of the quartz layer 212 at the location of the aperture 216 was etched away. The aperture 218 was fabricated by etching away substantially all of the chrome layer 214 at the location of the aperture 218 and a small portion of the quartz layer 212 at the location of the aperture 218. The aperture 220 was fabricated by etching away substantially all of the chrome layer 214 at the location of the aperture 220 and a portion of the quartz layer 212 at the location of the aperture 220. The quartz layer 212 was removed to a greater depth to form the aperture 220. The different depths and widths of the apertures 216, 218 and 220 as well as any defects that are developed in the mask, such as may occur during etching, for example, will have different effects on diffracting light that passes through the apertures 216, 218 and 220 and will similarly have different effects on shifting the phase of light that passes through the apertures 216, 218 and 220. Defects such as cracks 222 or fractures formed in the mask can also be propagated onto a wafer during a pattern transfer, which can adversely affect the performance of resulting chips.

In FIG. 3, light waves 302 are directed at a phase shift mask 304. The mask 304 includes a quartz substrate layer 306 through which the light waves 302 may pass and an opaque chrome layer 308, through which the light waves 302 may not pass. The mask 304 is designed to produce two desired features 310 and 312 on a photo resist 314. Some of the light waves 302 pass directly through an aperture 316 and expose a region 318 on the photo resist 314. Other of the light waves 302 are diffracted when they pass through the aperture 316. The diffraction is affected by factors including, but not limited to defects, such as cracks or fractures in the aperture, the wavelength of the light and the depth and/or width of the aperture 316. Dimensions of the apertures (e.g., depth, width) and defects (e.g., cracks, fractures) developed in portions of the mask defining the aperture 316 similarly affect the phase shifting of light passing there-through.

Wave 320 is for instance a light wave diffracted to the left while light wave 322 is a light wave diffracted to the right. Other of the light waves 302 pass through apertures 324 and 326. Again, the diffraction and phase shifting of the light passing through the apertures 324 and 326 is affected by defects, such as cracks or fractures and the dimensions (e.g., depth, width) of the apertures 324 and 326. For example light wave 328 passes directly through aperture 324 and interacts with diffracted light wave 320 at region 330, which due to a difference in phases between the light waves 320 and 328 causes total cancellation of the light waves 320 and 328, and thus the region 330 under aperture 324 is not exposed. Similarly, light wave 332 passes directly through aperture 326 and interacts with diffracted wave 322 at region 334 where cancellation occurs. Other cancellation occurs between waves diffracted through aperture 324 and aperture 316 at region 336 and between waves diffracted through aperture 326 and aperture 316 at region 338. Such cancellation enables square edges to be produced for the region 318. Thus, accurate pattern transfer is accomplished by precisely developing the region 318.

Turning to FIG. 4, the light waves 402 are directed at a mask 404 in which there are a plurality of apertures 406, 408, 410 and 412. The mask 404 includes a quartz layer 414 through which the light waves 402 may pass. The mask 404 also includes an opaque chrome layer 416 through which the light waves 402 may not pass. Some of the light waves 402 pass directly through the apertures 406, 408, 410 and 412, exposing regions on a photo resist 418 (e.g., regions 420 and 422) while other of the light waves 402 are diffracted by the apertures 406, 408, 410 and 412. As in FIG. 3, some of these light waves interact and cancel, such as for example at regions 424 and 426 thus facilitating smaller feature sizes with more precise shapes.

Figure 5:
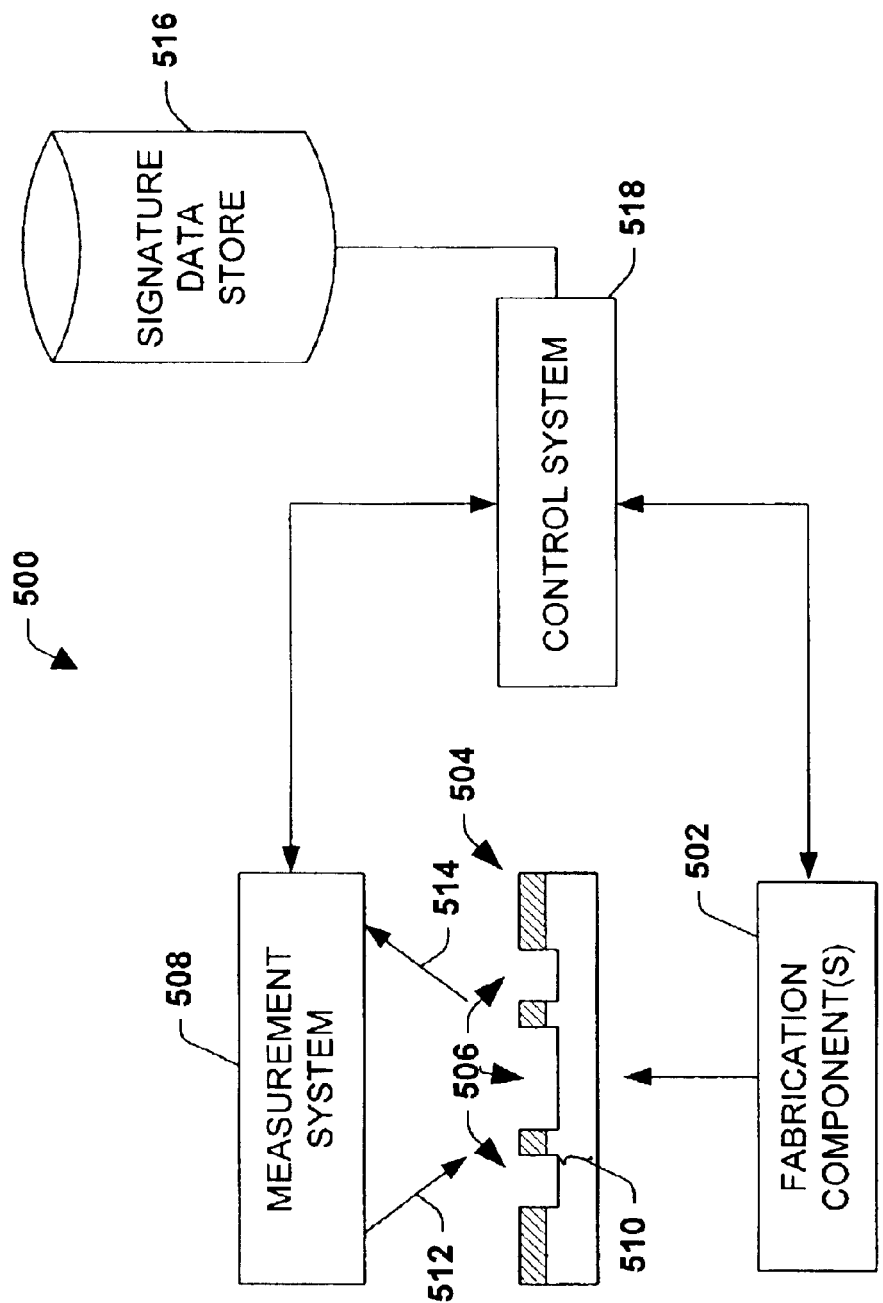
FIG. 5 is a block diagram illustrating a system for monitoring and controlling a phase shift fabrication process in accordance with one or more aspects of the present invention.

FIG. 5 illustrates a block diagram of a system 500 for monitoring and/or controlling a phase shift mask fabrication process according to one or more aspects of the present invention is illustrated. The system includes fabrication components 502 that operate on the mask 504. One such fabrication component may be an etching system, for example, that operates to form apertures 506 in the mask by, among other things, applying etchants to the mask. The system 500 also includes a measurement system 508 operable to detect defects such as cracks 510 or fractures developing in the mask, and to watch for or measure other developments in the process. For example, dimensions of apertures (e.g., depth, width, slope) forming in the mask can also be measured throughout the fabrication process. The measurement system 508 includes, for example, an acoustic source and/or a light source (not shown) that emits a sound and/or light beam 512 incident to the surface of the mask 504. The beam 512 is reflected 514 and /or passes through the mask and is altered thereby (e.g., diffracted, refracted, phase shifted, polarized, increased in magnitude, decreased in magnitude) according to defects 510 and/or apertures 506 formed in the mask 504. Beams that pass through the mask can be particularly useful in detecting subsurface defects, such as cracks or pinholes that may not be revealed by reflected beams. The measurement component 508 also includes a detection system (not shown) for detecting the reflected and/or diffracted beam 514. Defects 510 and/or dimensions of the apertures 506 can, for example, be determined based on scatterometry techniques. A scatterometry analysis can be performed, for example, that includes comparing (e.g., by pattern matching, interpolation or otherwise) one or more scatterometry signatures from the reflected and/or passed through beam 514 to one or more scatterometry signatures stored in a signature data store 516. Such signatures may be generated, for example, by combining phase, polarization and/or intensity information associated with the reflected and/or passed through beam 514. It is to be appreciated that the beam 512 can be directed at substantially all of the mask 504 simultaneously and/or at selected portions of the mask throughout the fabrication process to spot check portions of the mask, and to facilitate yielding determinations such as, for example, "defect present" or "defect free" at respective locations on the mask 504. Additionally, although the beam 512 is depicted as being directed at one side of the mask 504, it will be appreciated that the beam 512 can be directed at either and/or both sides of the mask 504.

The system 500 also includes a control system 518 operatively coupled to the fabrication components 502 and the measurement component 508. The control system 518 is programmed and/or configured to control the fabrication components and/or one or more operating parameters associated therewith based upon readings taken by the measurement system 508. By way of example, if it is determined that a crack is forming in the mask as apertures are being etched into the mask, then the control system can adjust the concentration, rate, and/or volume, for example, of etchants applied to the mask to mitigate exaggeration of the defect. It will be appreciated that a processor (not shown) may be included in the system, such as may be part of the controller, for example, to perform the functions described herein. The processor, or CPU, may be any of a plurality of suitable processors, and the manner in which the processor can be configured and/or programmed to carry out the functions described herein will be readily apparent to those having ordinary skill in the art based on the description provided herein.

As fabrication progresses, various signatures may be produced from the reflected and/or passed through beam(s) 514. The sequence in which such signatures are generated can be employed to determine, for example, the rate at which a defect 510 is forming, the depth at.which a defect is forming, the rate at which fabrication is progressing, times when fabrication may be substantially completed and/or times when an ex-situ quality control analysis may be appropriate. Analyzing the sequence of signatures, and the time required to produce transitions between such signatures can facilitate determining whether fabrication is progressing in an acceptable manner, can facilitate predicting optimal times to pause a fabrication process to probe the fabrication process and can facilitate determining if fabrication should be terminated, for example. Feedback/feed forward information can be generated from such sequence analysis to maintain, increase and/or decrease the rate at which fabrication processes (e.g., etching) progresses. For example, one or more etchant formulae and/or concentrations can be altered to affect the etching rate based on the signature sequence analysis.

By way of further example, if a severe defect (e.g., crack) is detected in the mask and/or if a detected defect affects the uniformity of an aperture to such a degree that it renders the mask unsuitable for its intended purpose and unsalvageable, then the mask can be discarded. It will be appreciated that the determination to discard the mask may based upon, for example, a programmed cost-benefit analysis, Bayesian system neural network, rule based expert system, etc. For example, if the cost of repairing or reducing the defect outweighs the benefit received from such repair, then it could be determined that it would be more cost and time effective to simply discard the mask 504. Additionally, or in the alternative, if it is not cost prohibitive to remedy the defect, the affected or damaged portions of the mask can be selectively marked, and the type of adjustments necessary to effect the repair can be determined. Nonlinear training systems can be utilized to determine the appropriate adjustments to make, for example, to mitigate and/or rectify the formation of the defect, and feedback/feed forward control data can be generated therefrom. By way of example, the rate, concentration and/or volume of etchants being applied to the mask can be adjusted according to control data to mitigate the continued formation of a crack in the mask during an etching process. Additionally, if a defect is detected below the surface of the mask, then the mask can be etched or polished back to reveal the defect and remedy the situation (e.g., polish away the defect, fill in the defect). Also, once a defect is detected, the system can focus in on the trouble spot to take additional measurements and obtain additional information.

As such, it will be appreciated that the system can implement historical/test data, such as may be stored within the data store 516, to facilitate decision making and/or utilize current measurements to control the fabrication process in real time. It is to be appreciated that, to effectively adapt the fabrication process to achieve desired results, various aspects of the invention can employ technologies associated with facilitating unconstrained optimization and/or minimization of error costs, such as, for example, non-linear training systems/methodologies including, but not limited to back propagation, Bayesian, fuzzy sets, non-linear regression, or other neural networking paradigms including mixture of expert systems, cerebella model arithmetic computer (CMACS), radial basis functions, directed search networks and function link networks.

In addition, the system 500 can be employed in populating the data store 516 in a training stage, for example. In a training mode, the system 500 can generate substantially unique scatterometry signatures, which are stored in the data store 516. The data store 516 can be populated by presenting a series of masks to the system, for instance. As such, the data store 516 can serve, for example, as a signal (signature) library that can be populated with an abundance of signatures against which one or more measurements can be compared. Alternatively, or in addition to manually observing values, simulation, modeling and/or artificial intelligence techniques can be employed to populate the data store with signatures against which measured values can be compared. It is to be appreciated that entries in the data store 516 can also, for example, be stored with/correlated with respective operating parameters under which they were obtained (e.g., illumination intensity, etchant concentration, etchant distribution volume/rate, temperature, pressure, timing parameters). As such, determinations made by comparing measurements to stored data can take into account the present value of one or more operating conditions such as temperature, pressure, etc. and the effects that these conditions are having on the fabrication process. It is to be further appreciated that the data store 516 can store data in data structures including, but not limited to one or more lists, arrays, tables, databases, stacks, heaps, linked lists and data cubes. It is also to be appreciated that many of the components of the system 500 including the data store can, for example, reside in one physical or logical device (e.g., computer, process) and/or may be distributed between two or more physical or logical devices (e.g, disk drives, tape drives, memory units). The system 500 can thus be employed to provide measurements of phase shift mask fabrication processes, and to control the processes in response thereto. The system 500 thus facilitates achieving higher quality masks that exhibit greater consistency with respect to phase shifting properties and accuracy of pattern transfers.

Figure 6:
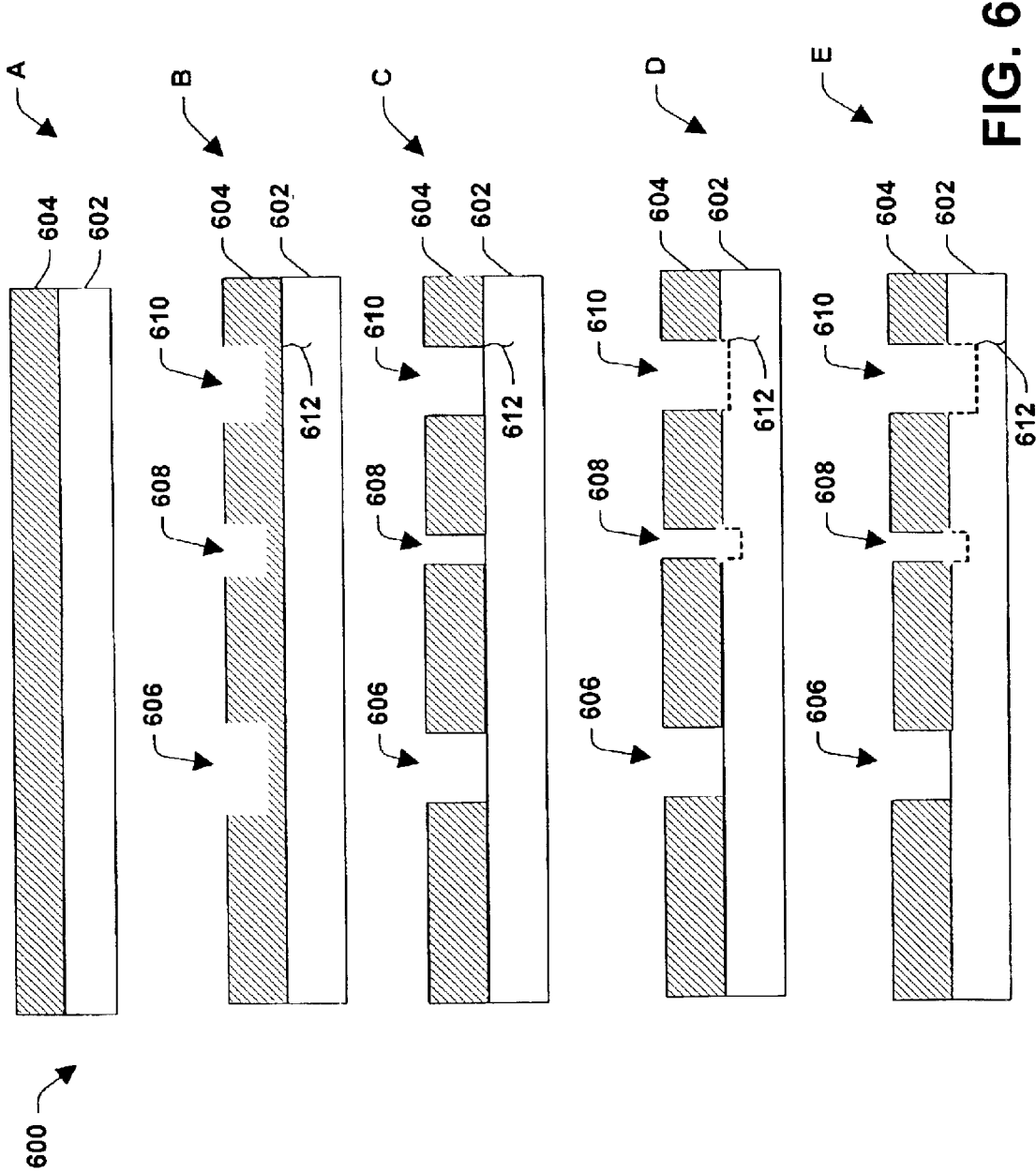
FIG. 6 illustrates a phase shift mask at different stages as it progresses through a fabrication process.

Turning now to FIG. 6, a phase shift mask 600 is illustrated at five different stages of a fabrication process. At stage A, a quartz layer 602 and a chrome layer 604 have been prepared for processing, but no apertures have been processed (e.g., etched) into either the quartz layer 602 or the chrome layer 604. At stage B, three apertures 606, 608 and 610 have been processed into the chrome layer 604. Aspects of the present invention facilitates monitoring the process for defects such as cracks 612 that may develop in the mask, and adapting the process in response to the monitored findings. Scatterometry techniques are employed in monitoring the process and can also be implemented to reveal the dimensions (e.g., depth, width, slope) of the apertures 606, 608 and 610 forming in the mask. According to aspects of the present invention, a determination can be made at stage B concerning, for example, whether the defect 612 is severe enough to warrant discarding the mask, whether progression of the crack can be halted by reducing the rate of etching, whether the crack is affecting the uniformity of aperture 610, whether transferring the defect onto a wafer would adversely affect a resulting chip, etc. At stage C, the mask 600 has been further processed to deepen the apertures 606, 608 and 610. Similar determinations can thus be made at stage C, including, for example, whether the crack 612 is increasing in size. At stage D, the mask 600 has been further processed to deepen the apertures 608 and 610, while the aperture 606 has not been further processed. As such, determinations can similarly be made at stage D with regard to the crack 612. At stage E, the mask 600 has been further processed to deepen the aperture 610, while the apertures 606 and 608 have not been further processed, and determinations regarding the crack 612 can once again be made. The present invention thus facilitates controlling a phase shift mask fabrication process in response to measurements taken during the process. Monitoring for defects in the mask and adapting the process in response thereto facilitates producing a mask that can achieve desired diffraction and/or phase shifting of light waves, with a resulting increase in the fidelity of image transfer.

Figure 7:
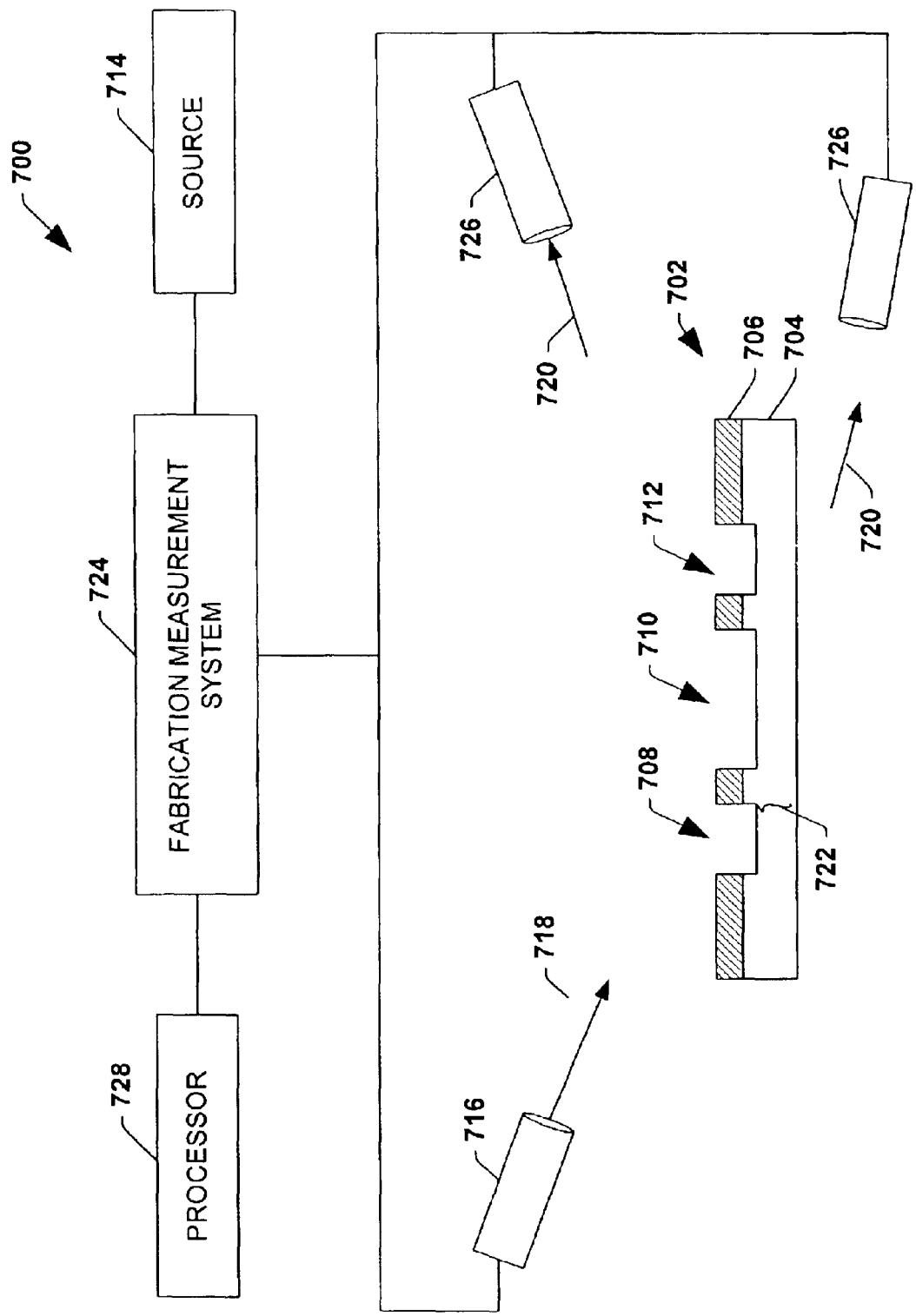
FIG. 7 illustrates a portion of a system effective to monitor the progress of a phase shift mask matriculating through a semiconductor fabrication process in accordance with one or more aspects of the present invention.

FIG. 7 illustrates a portion of a system 700 being employed to monitor (e.g., via scatterometry) the fabrication of a phase shift mask 702 according to one or more aspects of the present invention. It will be appreciated that only a small portion of the mask 702 is depicted in FIG. 7 for purposes of simplicity. The mask 702 is illustrated as including a substantially transparent layer 704 (e.g., quartz) and a substantially opaque layer 706 (e.g., chrome), and as having three apertures 708, 710, 712 processed (e.g., etched) therein. It is to be appreciated that while two layers and three apertures are depicted, the mask 702 can have any number of layers and apertures formed therein. Furthermore, while the substantially transparent layer 704 may be quartz and the substantially opaque layer 706 may be chrome, it will be appreciated that other substantially transparent layers and other substantially opaque layers may be employed.

A source 714 of light (e.g., a laser) and/or sound provides light and/or acoustic waves to one or more emitters 716 that direct a beam 718 incident to the mask 702. The beam 718 passes through or is reflected 720 from the mask 702, partially or entirely. For example, some waves of an acoustic beam may pass through the mask, while other waves of the acoustic beam may be reflected off of the surface of the mask. Similarly, all of a beam of light directed at the mask may be reflected off of the mask's surface as little to none of the light penetrates the mask. Regardless of whether the beam is reflected and/or passes through the mask, the features of the mask, such as a crack 722 that may develop in the mask, affect the beam. The incident beam 718 may be referred to as the reference beam, and thus the properties (e.g., phase, angle, intensity, polarization, wavelength and/or magnitude) of the reference beam 718, which will vary in accordance with the evolving dimensions of the apertures 708, 710, 712 and/or defects 722 in the mask 702, may be recorded in a measurement system 724 to facilitate later comparisons to the reflected beam 720 (e.g., via signature comparison). One or more light detecting components 726 collect the reflected and/or passed through beam 720 and transmit the collected beam, and/or data associated therewith to the measurement system 724.

The measurement system forwards this information to a processor 728, which may or may not be integral with the measurement system 724. The processor 728, or central processing unit (CPU), is programmed to control and carry out the various functions described herein. The processor 728 may be any of a plurality of processors, and the manner in which the processor can be programmed to carry out the functions described herein will be readily apparent to those having ordinary skill in the art based on the description provided herein. The reflected and/or passed through beam 720 can, for example, be analyzed to generate one or more signatures that can be compared to one or more stored signatures to determine whether the process is proceeding as planned (e.g., whether the size of the crack qualifies it as a significant or an insignificant defect, whether the defect is formed substantially below the surface of the mask, whether the apertures have been processed to a sufficient depth), and thus whether, for example, feed forward and/or backward information should be generated and applied to selectively adjust one or more operating parameters of one or more IC fabrication components (e.g., photolithography, etching) to adapt the process and facilitate achieving a desired result.

Figure 8:
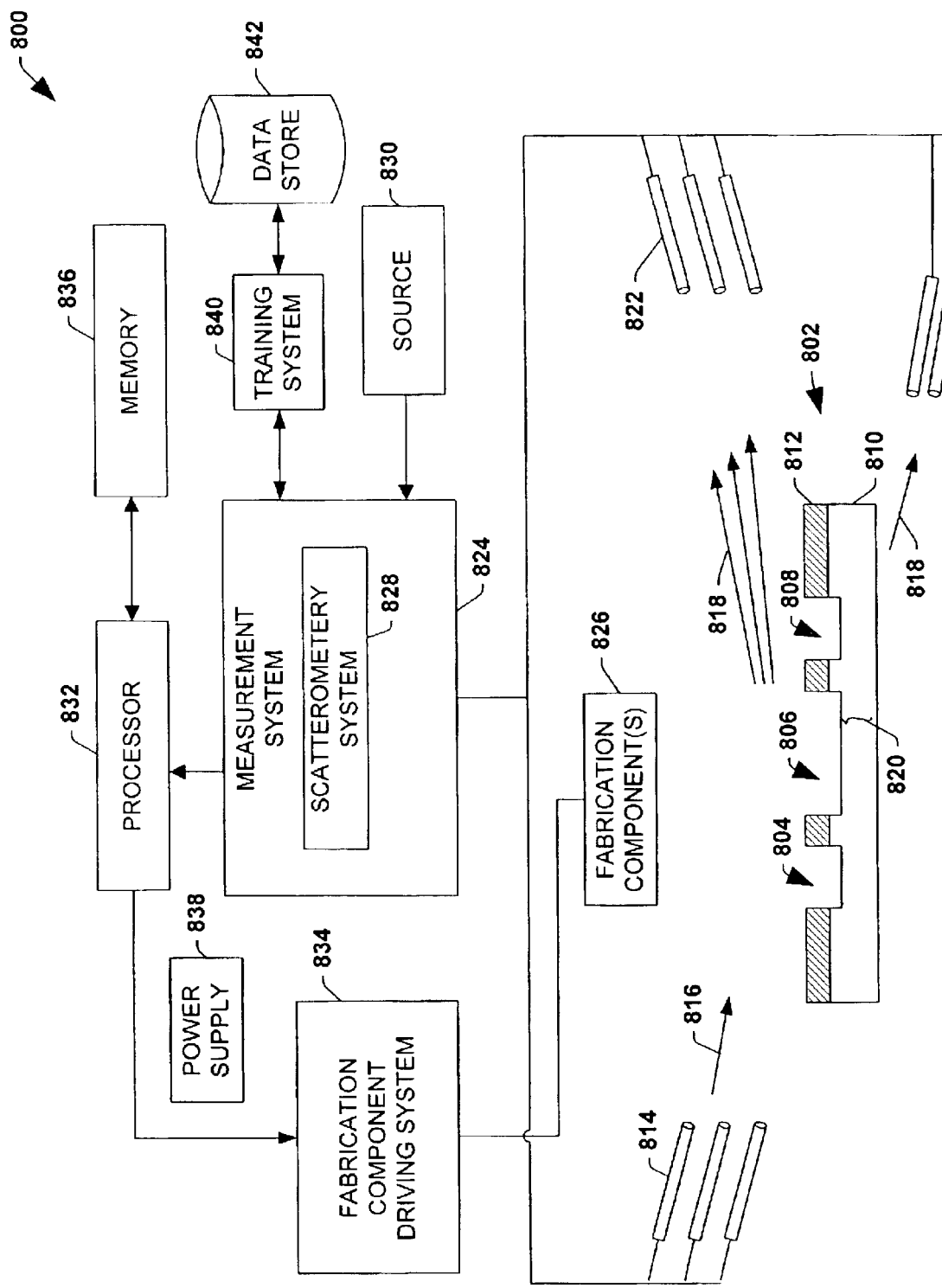
FIG. 8 illustrates a system for monitoring and controlling a phase shift mask fabrication process according to one or more aspects of the present invention.

Turning to FIG. 8, a system 800 for monitoring and controlling a phase shift mask fabrication process according to one or more aspects of the present invention is illustrated. A phase shift mask 802, or a portion thereof, is depicted as undergoing the fabrication process and has apertures 804, 806, 808 processed (e.g., etched) therein. The apertures are formed within a substantially transparent layer 810 (e.g., quartz) and a substantially opaque layer 812 (e.g., chrome) of the mask 802, and facilitate pattern transfers and selective phase shifting of light that passes thought the mask (e.g., as depends upon the respective dimensions, such as depth and width, of the apertures).

One or more emission sources 814 project a beam 816 of light and or acoustic waves onto the mask 802. The beam 816 interacts with the mask 802 and is reflected and/or passes through 818 the mask whereby it is altered in different, quantifiable manners (e.g., diffracted, refracted, phase shifted, polarized, increased in magnitude, decreased in magnitude) in accordance with defects such as cracks 820 in the mask as well as the dimensions (e.g., depth, width) of other features such as the apertures 804, 806, 808 formed in the mask 802. Beams that pass through the mask can be particularly useful in detecting subsurface defects, such as cracks or pinholes that may not be revealed by reflected beams. The reflected and/or passed through beam 818 is collected by one or more light detecting components 822, and processed by a measurement system 824. The reflected and/or passed through beam 818 may, for example, be processed to generate signatures, which can be utilized to facilitate feedback and/or feed-forward control of one or more fabrication components 826 and/or operating parameters associated therewith as described herein to achieve a desired result.

The measurement system 824 includes a scatterometry system 828, which can be any scatterometry system suitable for carrying out aspects of the present invention as described herein. A source 830 of light (e.g., a laser) and/or acoustic or ultrasonic sound provides signal(s) necessary to establish the beam 816 to the one or more emission sources 814 via the measurement system 824. To generate a light beam, for example, the source 830 can be a frequency stabilized laser, laser diode or helium neon (HeNe) gas laser. Similarly, any one or more light and/or acoustic detecting components 822 suitable for carrying out aspects of the present invention may be employed (e.g., photo detector, photo diodes, microphone) for collecting the reflected and/or passed through beam 818.

A processor 832 receives the measured data from the measurement system 824 and is programmed to control and operate the various components within the system 800 in order to carry out the various functions described herein. The processor, or CPU 832, may be any of a plurality of processors, and the manner in which the processor 832 can be programmed to carry out the functions described herein will be readily apparent lo those having ordinary skill in the art based on the description provided herein.

The processor 832 is also coupled to a fabrication component driving system 834 that drives one or more of the fabrication components 826. The processor 832 controls the fabrication component driving system 834 to selectively control one or more of the fabrication components 826 and/or one or more operating parameters associated therewith as described herein. For example, the rate, concentration and/or volume of etchants applied by an etching component can be selectively adjusted to alter the rate of etching and thereby mitigate the progression of a crack 820 forming in the mask 802. The processor 832 monitors the process via the signatures generated by the reflected and/or passed through beam, and selectively regulates the fabrication process by controlling the corresponding fabrication components 826. Such regulation facilitates adapting an existing fabrication process and further facilitates initiating a subsequent fabrication process based, at least in part, upon relevant historical data.

A memory 836 is also shown in the example illustrated in FIG. 8. The memory 836 is operable to store, among other things, program code executed by the processor 832 for carrying out one or more of the functions described herein. The memory may include, for example, read only memory (ROM) and random access memory (RAM). The RAM is the main memory into which the operating system and application programs arc loaded. The memory 836 may also serve as a storage medium for temporarily storing information and data that may be useful in carrying out one or more aspects of the present invention. For mass data storage, the memory 836 may also include a hard disk drive (e.g., 50 Gigabyte hard drive).

A power supply 838 is included to provide operating power to one or more components of the system 800. Any suitable power supply 836 (e.g., battery, line power) can be employed to carry out the present invention.

A training system 840 may also be included. The training system 840 may be adapted to populate a data store 842 (which may be comprised within the memory 836) for use in subsequent monitoring. For example, the scatterometry system 828 can generate substantially unique scatterometry signatures that can be stored in the data store 842 via the training system 840. The data store 842 can be populated with an abundance of scatterometry signatures by examining a series of masks. Scatterometry signatures can be compared to scatterometry measurements stored in the data store 842 to generate feed forward/backward control data that can be employed to control the fabrication process. It is to be appreciated that the data store 842 can store data in data structures including, but not limited to one or more lists, arrays, tables, databases, stacks, heaps, linked lists and data cubes. Furthermore, the data store 842 can reside on one physical device and/or may be distributed between two or more physical devices (e.g., disk drives, tape drives, memory units).

Turning now to FIGS. 9–11 a chuck 902 is shown in perspective supporting a phase shift mask 904 whereupon one or more features, including apertures and/or defects may be located. The mask 904 may be logically partitioned into a grid pattern as shown in FIG. 10 to facilitate scanning and monitoring the mask as it matriculates through a fabrication process. Each grid block (XY) of the grid pattern corresponds to a particular portion of the mask 904, and each grid block may have one or more apertures and/or defects (e.g., cracks) associated with that grid block. The mask can be scanned so that portions can be individually monitored with scatterometry based techniques for properties including, but not limited to, the presence of a defect such as a crack, crack length, aperture width, aperture depth, etc. This may facilitate selectively determining to what extent, if any, fabrication adjustments are necessary. Obtaining such information may also assist in determining problem areas associated with fabrication processes.

In FIG. 10, respective plots are illustrated for measurements taken via scatterometry based techniques at portions of a phase shift mask 904 corresponding to grid mapped locations of the mask ($X_1Y_1 \ldots X_{12},Y_{12}$). The plots can, for example, be signatures indicating whether one or more defects are forming in the mask. Given the values depicted in FIG. 10, it may be determined that an undesirable condition exists at one or more locations on the mask 904. For instance, the measurement at coordinate $X_7Y_6$ yields a plot that is substantially higher than the respective measurements of the other portions XY. This can be indicative of a defect forming at that location and/or of apertures forming outside of acceptable tolerances. As such, fabrication components and/or operating parameters associated therewith can be adjusted accordingly to mitigate this condition as well as to mitigate repeating this situation on subsequently processed masks. For example, etching components may be driven so as to increase or decrease the rate of etching and/or to change the direction of etching to mitigate the progression of a crack forming in the mask, for example. It is to be appreciated that although FIG. 10 illustrates the mask 904 being mapped (partitioned) into 144 grid block portions, the mask 904 may be mapped with any suitable number of portions to effect desired monitoring and control. Additionally, while the discussion of FIG. 10 mentions etching, it is to be appreciated that the present invention may be employed with other mask fabrication stages, and that etching is merely illustrative, and is not intended to be limiting.

FIG. 11 illustrates a table of acceptable and unacceptable signature values. As can be seen, all the grid blocks, except grid block $X_7Y_6$, have measurement values corresponding to an acceptable value ($V_A$), while grid block $X_7Y_6$ has an undesired value ($V_U$). Thus, it has been determined that an undesirable fabrication condition exists at the portion of the mask 904 mapped by grid block $X_7Y_6$. Accordingly, fabrication process components and parameters may be adjusted as described herein to adapt the fabrication process accordingly to mitigate the re-occurrence or persistence of this condition. Alternatively, the value at block $X_7Y_6$ may be indicative of an unacceptable condition such as a defect or crack that is so significant that it warrants discarding the mask.

Figure 12:
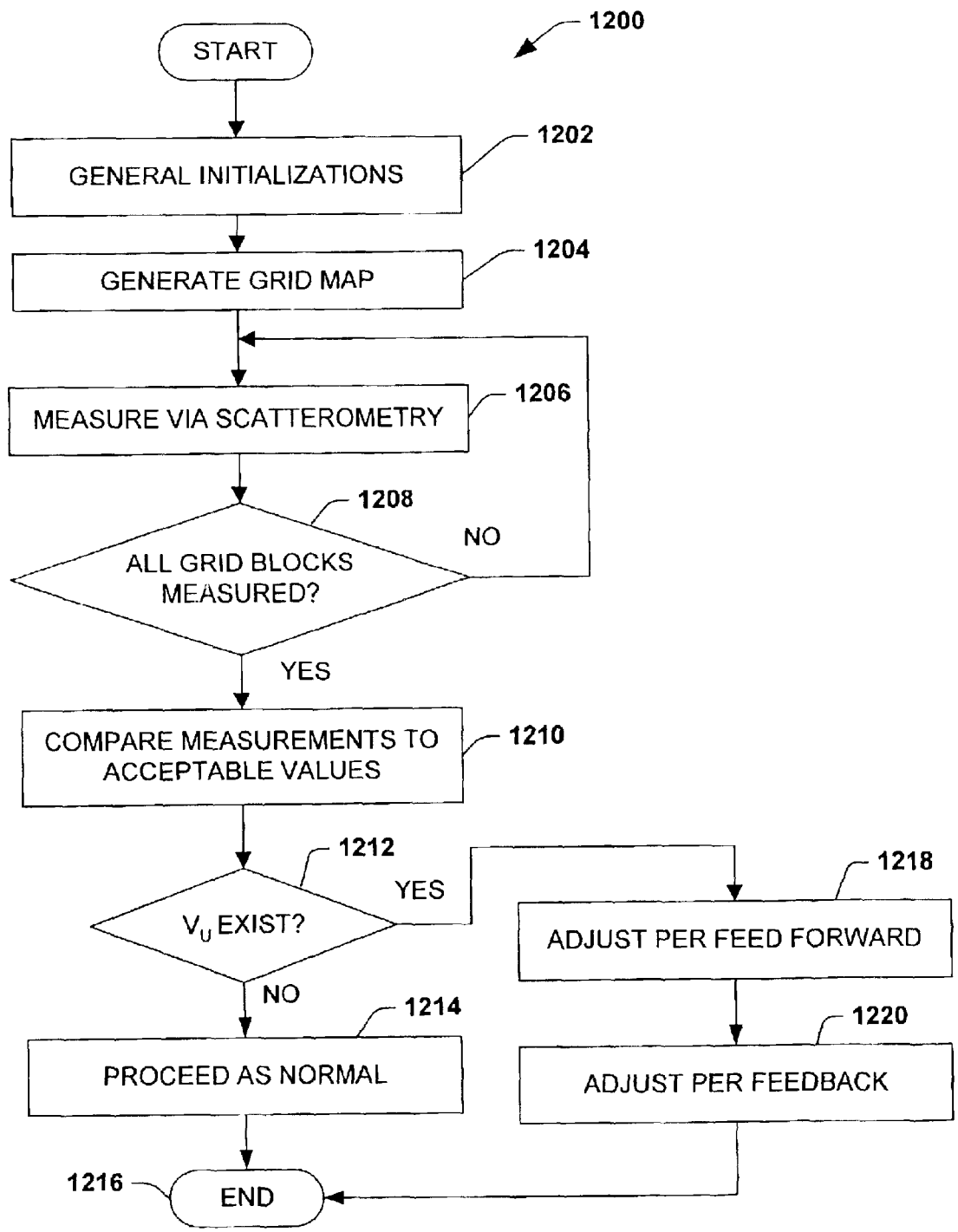
FIG. 12 is flow diagram illustrating a methodology for monitoring and controlling a phase shift mask fabrication process according to one or more aspects of the present invention.

In view of the exemplary systems shown and described above, a methodology, which may be implemented in accordance with one or more aspects of the present invention, will be better appreciated with reference to the flow diagram of FIG. 12. While, for purposes of simplicity of explanation, the methodology is shown and described as a series of function blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with one or more aspects of the present invention. It is to be appreciated that the various blocks may be implemented via software, hardware a combination thereof or any other suitable means (e.g., device, system, process, component) for carrying out the functionality associated with the blocks. It is also to be appreciated that the blocks are merely to illustrate certain aspects of the present invention in a simplified form and that these aspects may be illustrated via a lesser and/or greater number of blocks.

FIG. 12 is flow diagram illustrating a methodology 1200 for monitoring and controlling an phase shift mask fabrication process according to one or more aspects of the present invention. The methodology begins at 1202 wherein general initializations are performed. Such initializations can include, but are not limited to, establishing pointers, allocating memory, setting variables, establishing communication channels and/or instantiating one or more objects. At 1204, a grid map comprising one or more grid blocks "XY" is generated. Such grid blocks may correspond locations on the mask where apertures are formed and/or where defects such as fractures are likely to form, for example. At 1206, as the mask matriculates through the fabrication process, measurements are taken at the grid mapped locations, such as with scatterometry based techniques. For example, as apertures are processed (e.g., etched) into the mask, dimensions (e.g., depth, width) of the apertures can be measured at the respective grid mapped locations. Additionally, the presence or formation of defects such as cracks in the wafer can be monitored for at the grid mapped locations. At 1208, a determination is made as to whether measurements have been taken at all (or a sufficient number) of grid mapped locations. If the determination at 1208 is NO, then processing returns to 1206 so that additional measurements can be made. If the determination at 1208 is YES, then at 1210 the measurements are compared to acceptable values to determine if the fabrication process is progressing as planned. By way of example, the measurements can be compared to acceptable values to determine if, for example, defects such as cracks are forming at the grid mapped locations and/or if the apertures are being formed uniformly. Additionally, or in the alternative, the measurements can be analyzed to produce respective signatures to serve as the basis for such determinations. These signatures can be compared to acceptable signature values for respective grid mapped locations. At 1212, a determination is made as to whether an undesired value ($V_U$) has been encountered at any one or more of the grid mapped locations (e.g., indicating that a defect has been detected. If the determination at 1212 is NO, then at 1214 processing continues as normal. The methodology can thereafter advance to 1216 and end. If, however, the determination at 1212 is YES, meaning that an undesired value was encountered, then at 1218, one or more fabrications components and/or operating parameters associated therewith can be selectively adjusted as described herein according to feed forward control data derived from the measurements to mitigate or remedy the situation. For example, data generated by sophisticated modeling techniques can be fed forward to an etching stage to adjust the concentration, rate and/or volume of etchants applied to the mask to regulate the rate of etching and adapt aperture formation. Alternatively, or in addition, if the undesired value exceeds some threshold, a decision can be made to discard the mask. For example, if the value indicates that a very substantial crack has formed in the mask which is beyond repair, then the mask can be scrapped. At 1220, control data derived from the measurements can also be feed back to adjust one or more fabrications components and/or operating parameters associated therewith to mitigate re-occurrence of the undesired event during subsequent processing. For instance, etching parameters can be adjusted to facilitate proper formation of apertures on subsequently processed masks. The methodology then ends at 1216. As mentioned above, events can occur in orders different from that depicted in FIG. 12. For example, measurements taken, as at 1206, can be compared to acceptable values, as at 1210, prior to determining whether measurements have been taken at all grid mapped locations, as at 1208.

Figure 13:
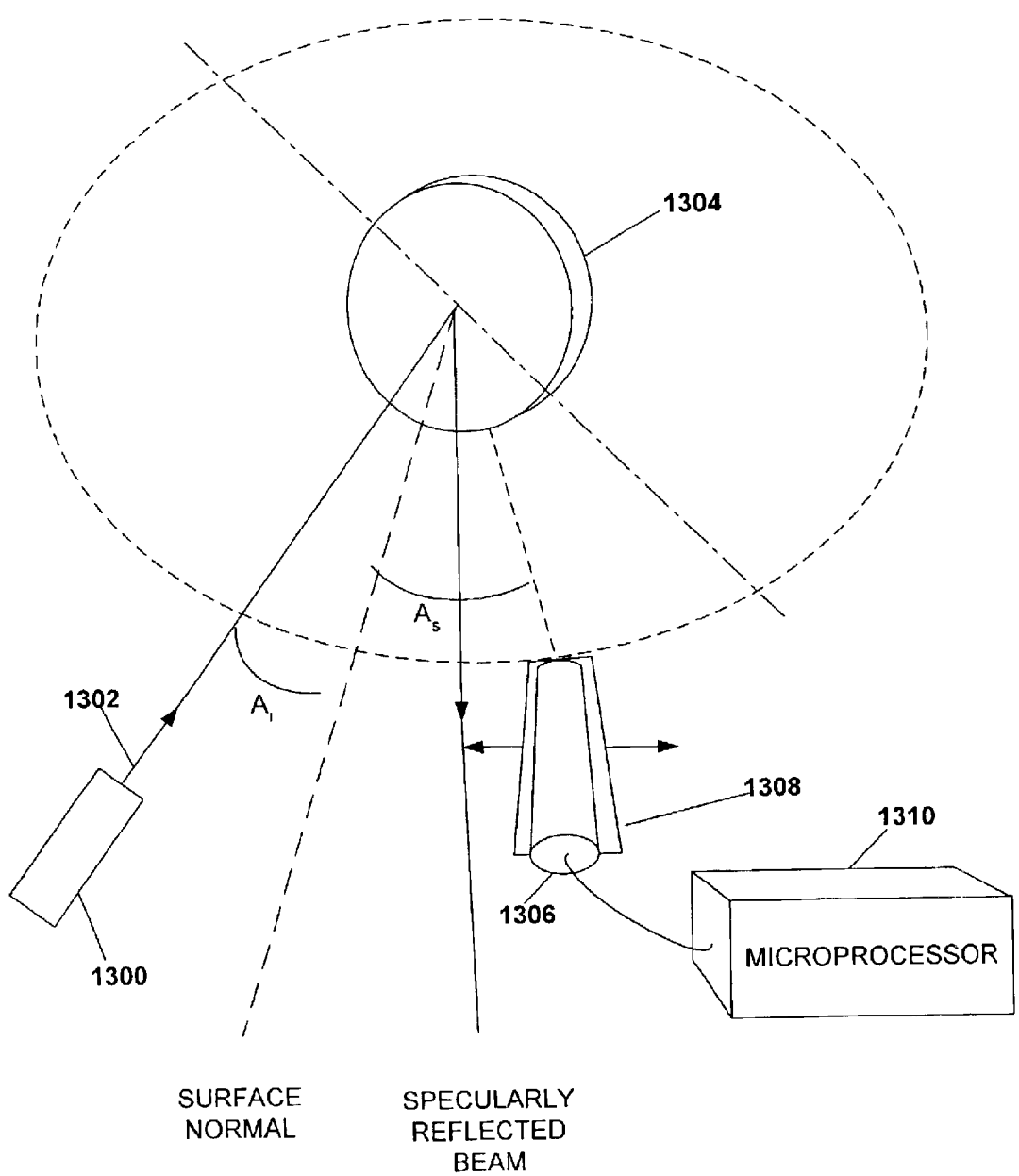
FIG. 13 illustrates an exemplary scatterometry system suitable for implementation with one or more aspects of the present invention.

FIG. 13 illustrates an exemplary scatterometry system suitable for implementation with one or more aspects of the present invention. Light from a laser 1302 is brought to focus in any suitable manner to form a beam 1304. A sample, such as a phase shift mask 1306, is placed in the path of the beam 1304 and a photo detector or photo multiplier 1308 of any suitable construction. Different detector methods and arrangements may be employed to determine the scattered and/or reflected power. A microprocessor 1310, of any suitable design, may be used to process detector readouts, including, but not limited to, intensity properties of the specularly reflected light, polarization properties of the specularly reflected light, and angular locations of different diffracted orders. Thus, light reflected from the sample 1306 may be accurately measured.

Concepts of scatterometry and how they are employed in accordance with one or more aspects of the present invention are discussed with respect to FIGS. 14–19. Scatterometry is a technique for extracting information about a surface upon which an incident light has been directed. Scatterometry is a metrology that relates the geometry of a sample to its scattering effects. Scatterometry is based optical diffraction responses. Scatterometry can be employed to acquire information concerning properties including, but not limited to, horizontal/vertical alignment/shifting/compression/stretching, dishing, erosion, profile and critical dimensions of a surface and/or features present on a surface. The information can be extracted by comparing the phase and/or intensity of a reference light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the planarity of the surface, features on the surface, voids in the surface, the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique intensity/phase signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk,$$

where j is an imaginary number.

The signal (signature) library can be constructed from observed intensity/phase signatures and/or signatures generated by modeling and simulation. By way of illustration, when exposed to a first incident light of known intensity, wavelength and phase, a wafer can generate a first intensity/phase signature. Observed signatures can be combined with simulated and modeled signatures to form a signal (signature) library. Simulation and modeling can be employed to produce signatures against which measured intensity/phase signatures can be matched. In one exemplary aspect of the present invention, simulation, modeling and observed signatures are stored in a signal (signature) data store. Thus, when intensity/phase signals are received from scatterometry detecting components, the intensity/phase signals can be pattern matched, for example, to the library of signals to determine whether the signals correspond to a stored signature.

Figure 14:
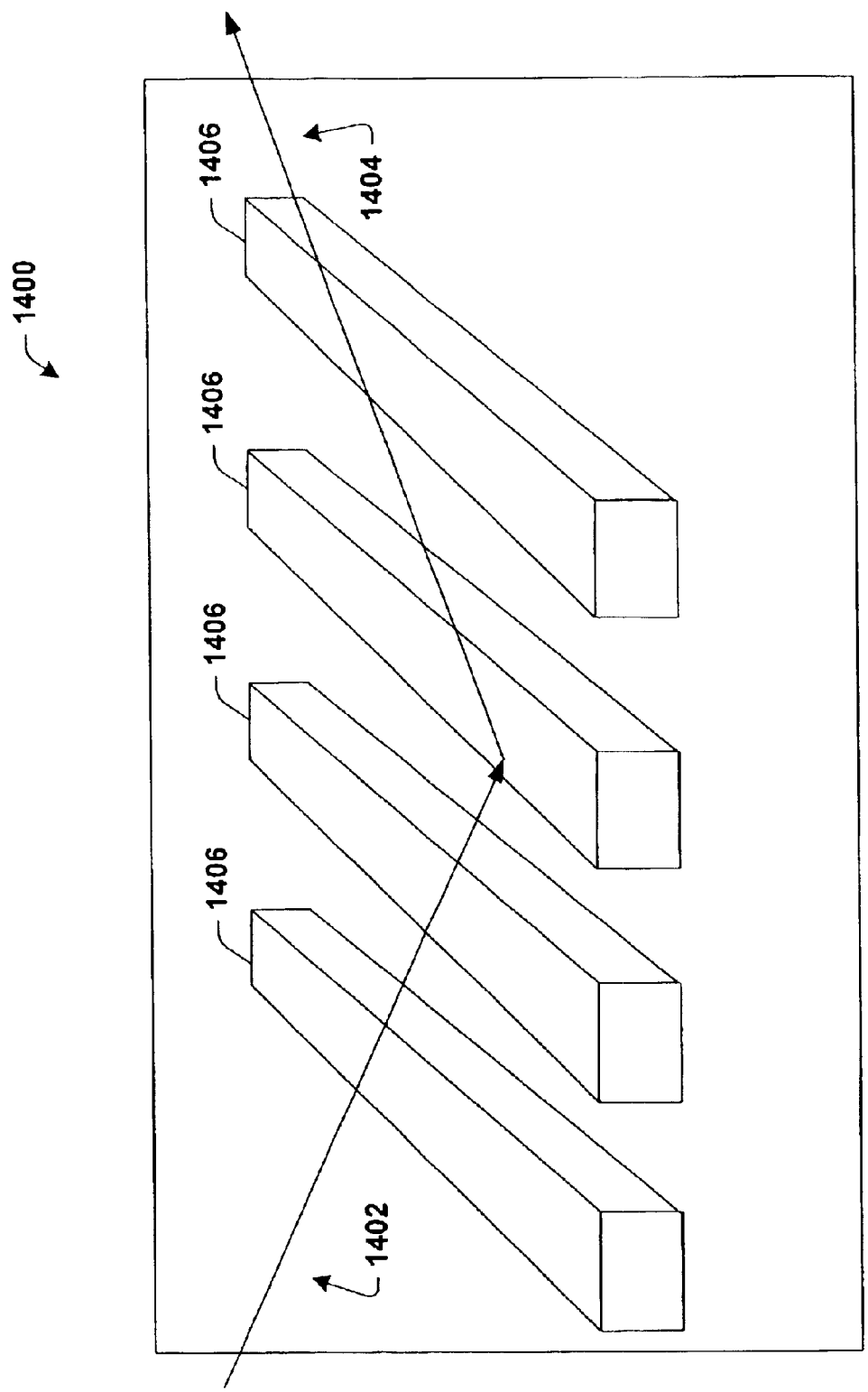
FIG. 14 is a simplified perspective view of an incident light reflecting off a surface in accordance with one or more aspects of the present invention.

To illustrate the principles described above, reference is now made to FIGS. 14 through 19. Referring initially to FIG. 14, an incident light 1402 is directed at a surface 1400, upon which one or more features 1406 may exist. The incident light 1402 is reflected as reflected light 1404. The properties of the surface 1400, including but not limited to, thickness, uniformity, planarity, chemical composition and the presence of features, can affect the reflected light 1404. The features 1406 are raised upon the surface 1400, but could also be recessed therein. The phase and/or intensity of the reflected light 1404 can be measured and plotted, as partially shown, for example, in FIG. 19. Such plots can be employed to compare measured signals with signatures stored in a signature library using techniques like pattern matching, for example.

Figure 15:
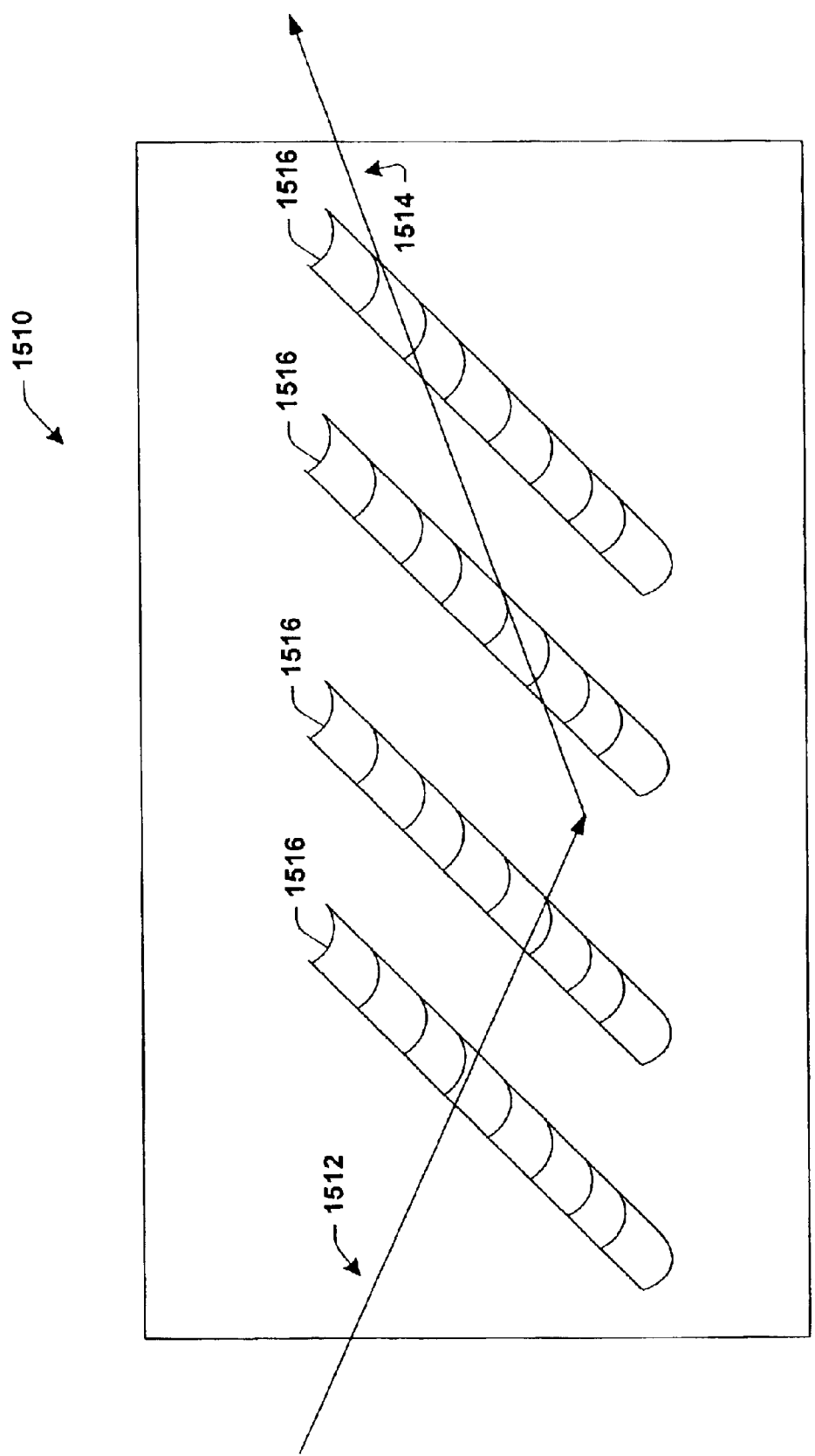
FIG. 15 is another simplified perspective view of an incident light reflecting off a surface in accordance with one or more aspects of the present invention.

Referring now to FIG. 15, an incident light 1512 is directed onto a surface 1510 upon which one or more depressions 1518 appear. The incident light 1512 is reflected as reflected light 1514. Depressions 1518 will affect the scatterometry signature to produce a substantially unique signature. It is to be appreciated that scatterometry can be employed to measure, among other things, features appearing on a surface, features appearing in a surface, features emerging in a pattern.

Figure 16:
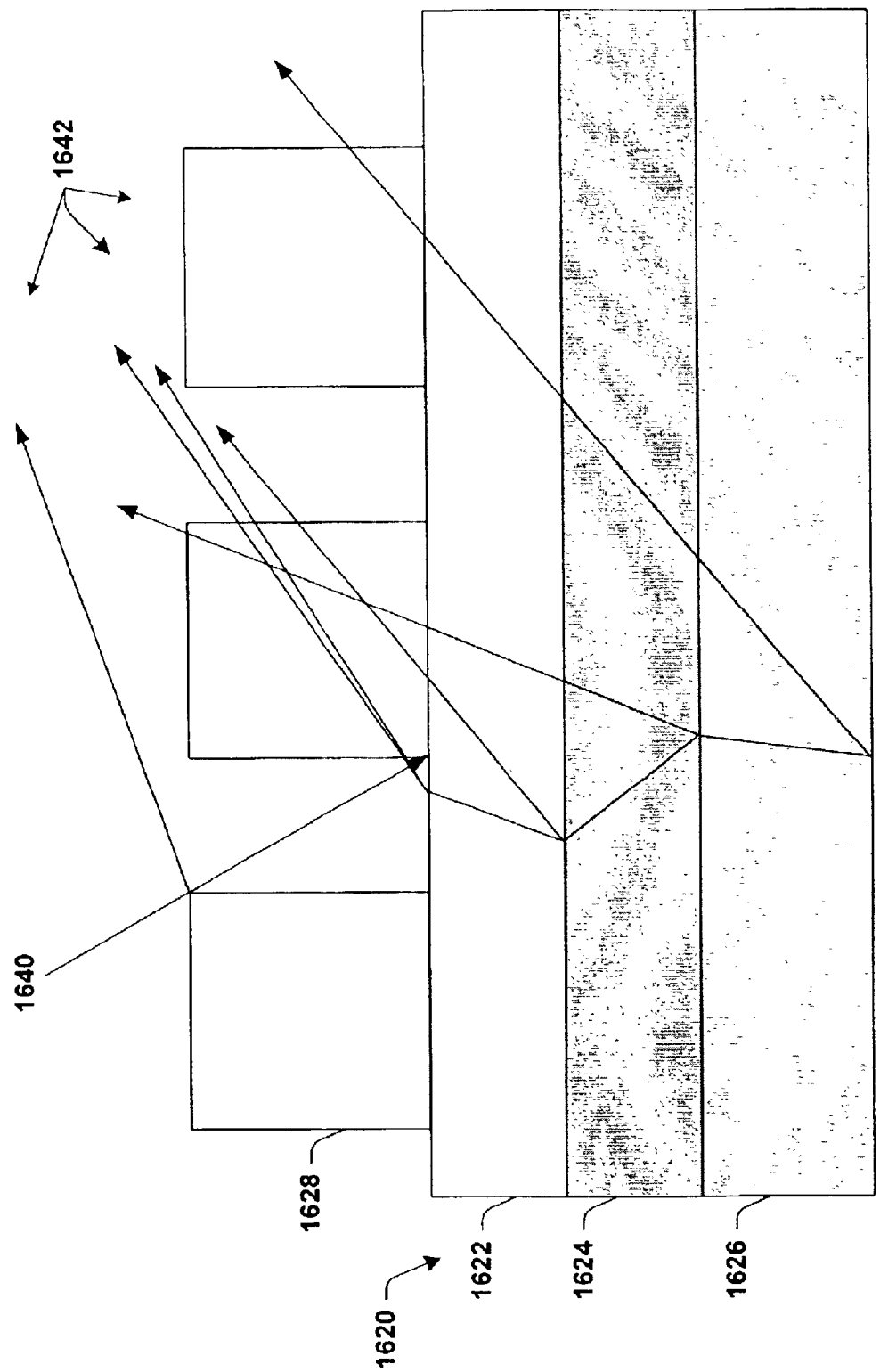
FIG. 16 illustrates a complex reflected and refracted light produced when an incident light is directed onto a surface in accordance with one or more aspects of the present invention.

Turning now to FIG. 16, complex reflections and refractions of an incident light 1640 are illustrated. The reflection and refraction of the incident light 1640 can be affected by factors including, but not limited to, the presence of one or more features 1628 and the composition of the substrate 1620 upon which the features 1628 reside. For example, properties of the substrate 1620 including, but not limited to the thickness of a layer 1622, the chemical properties of the layer 1622, the opacity and/or reflectivity of the layer 1622, the thickness of a layer 1624, the chemical properties of the layer 1624, the opacity and/or reflectivity of the layer 1624, the thickness of a layer 1626, the chemical properties of the layer 1626, and the opacity and/or reflectivity of the layer 1626 can affect the reflection and/or refraction of the incident light 1640. Thus, a complex reflected and/or refracted light 1642 may result from the incident light 1640 interacting with the features 1628, and/or the layers 1622, 1624 and 1626. Although three layers 1622, 1624 and 1626 are illustrated in FIG. 16, it is to be appreciated that a substrate can be formed of a greater or lesser number of such layers.

Figure 17:
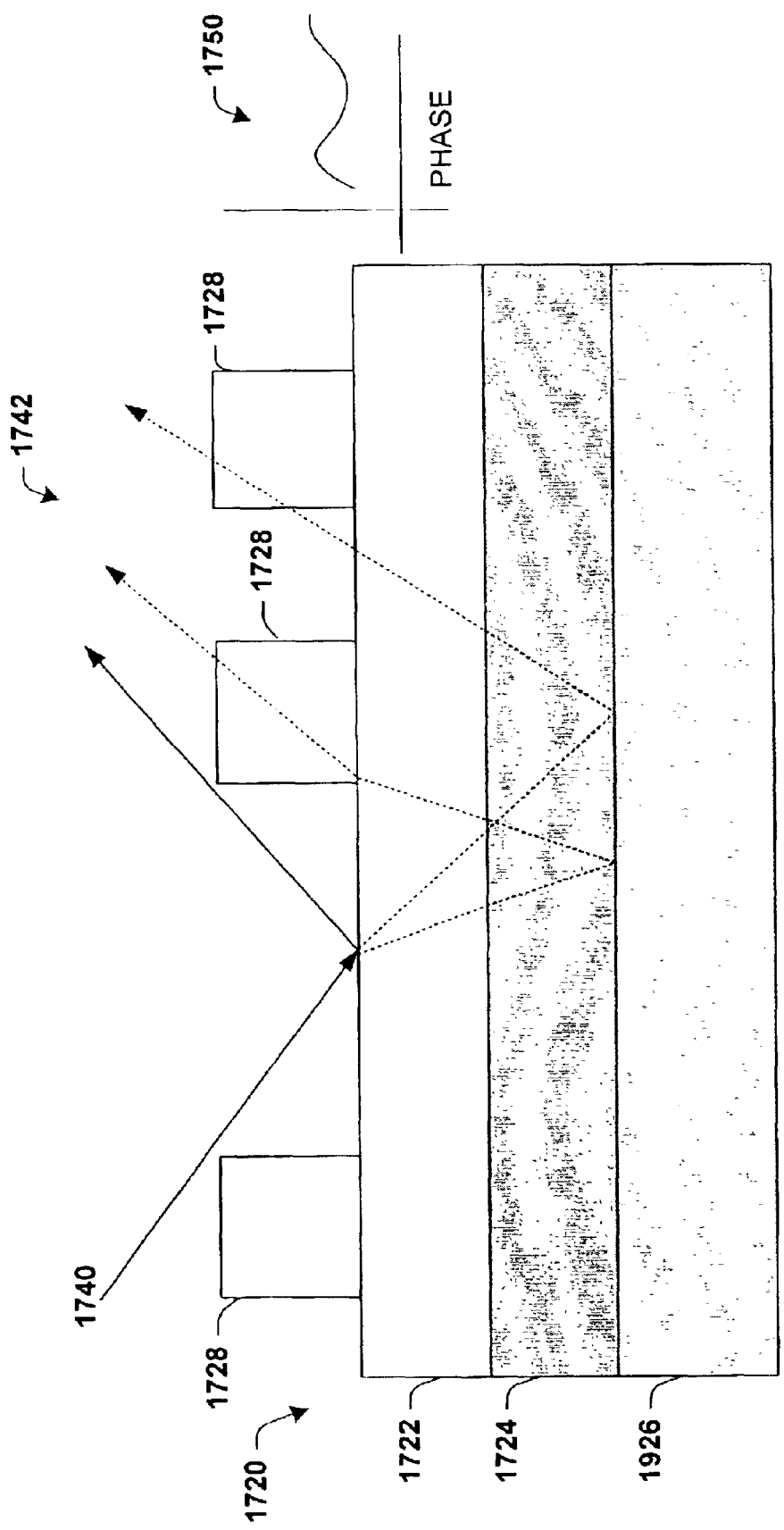
FIG. 17 illustrates another complex reflected and refracted light produced when an incident light is directed onto a surface in accordance with one or more aspects of the present invention.
Figure 18:
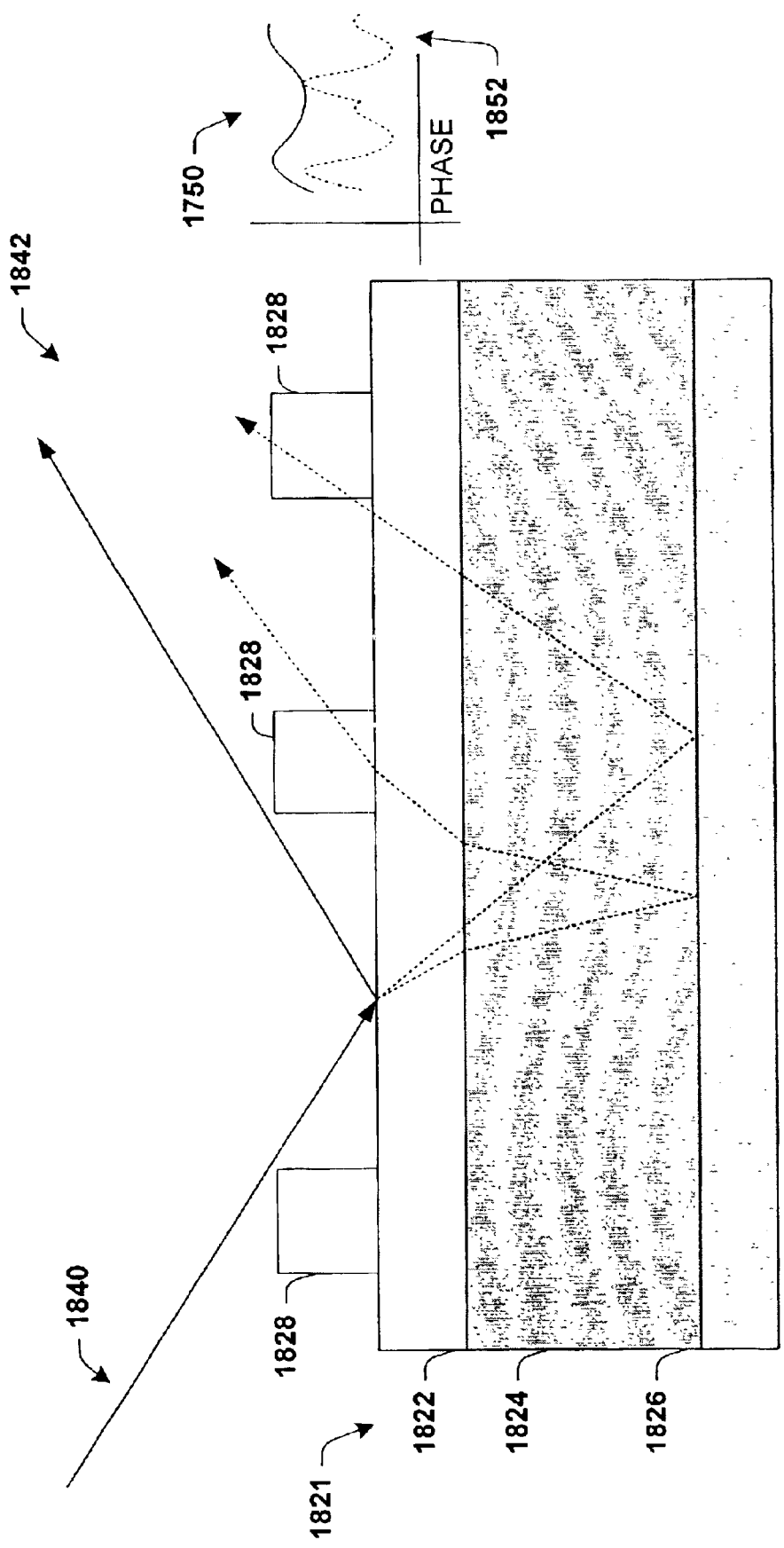
FIG. 18 illustrates yet another complex reflected and refracted light produced when an incident light is directed onto a surface in accordance with one or more aspects of the present invention.
Figure 19:
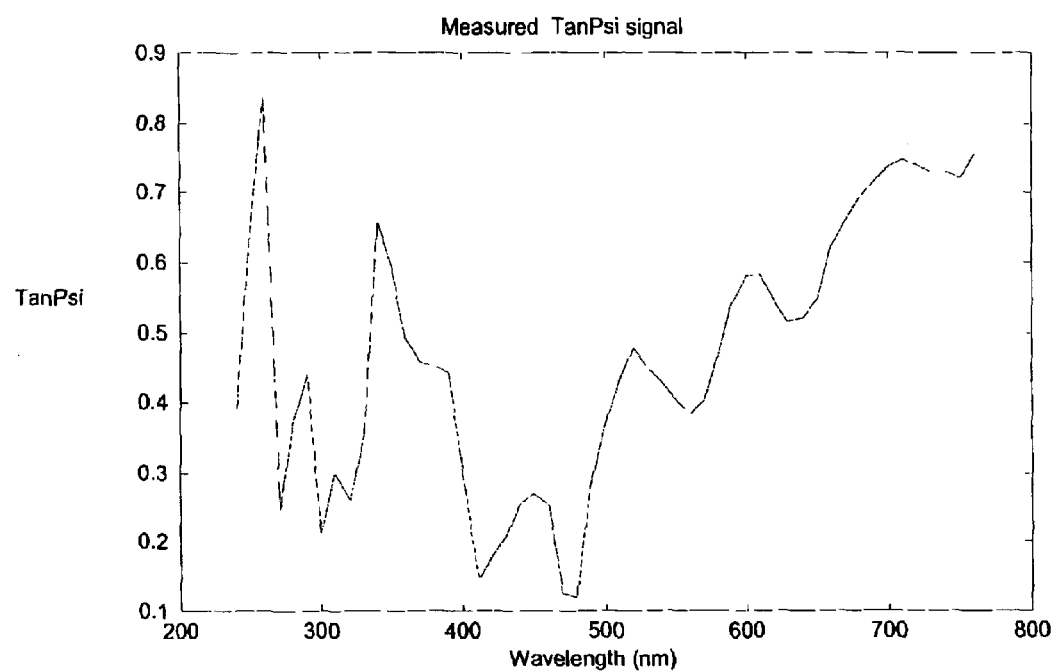
FIG. 19 illustrates phase and/or intensity signals recorded from a complex reflected and refracted light produced when an incident light is directed onto a surface in accordance with one or more aspects of the present invention.
Figure 19:
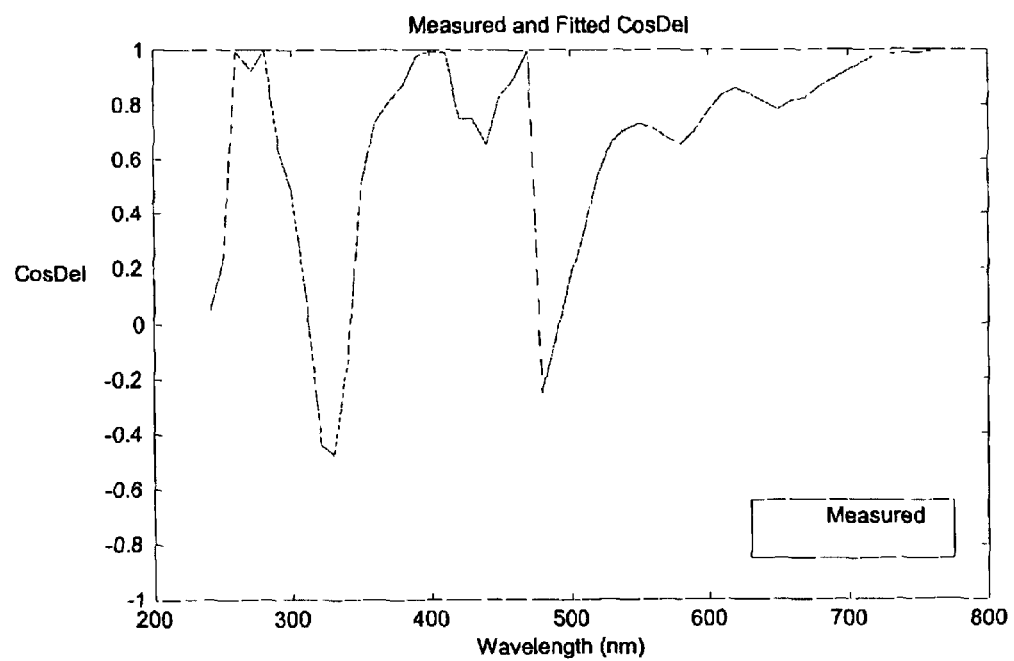
Figure 20:
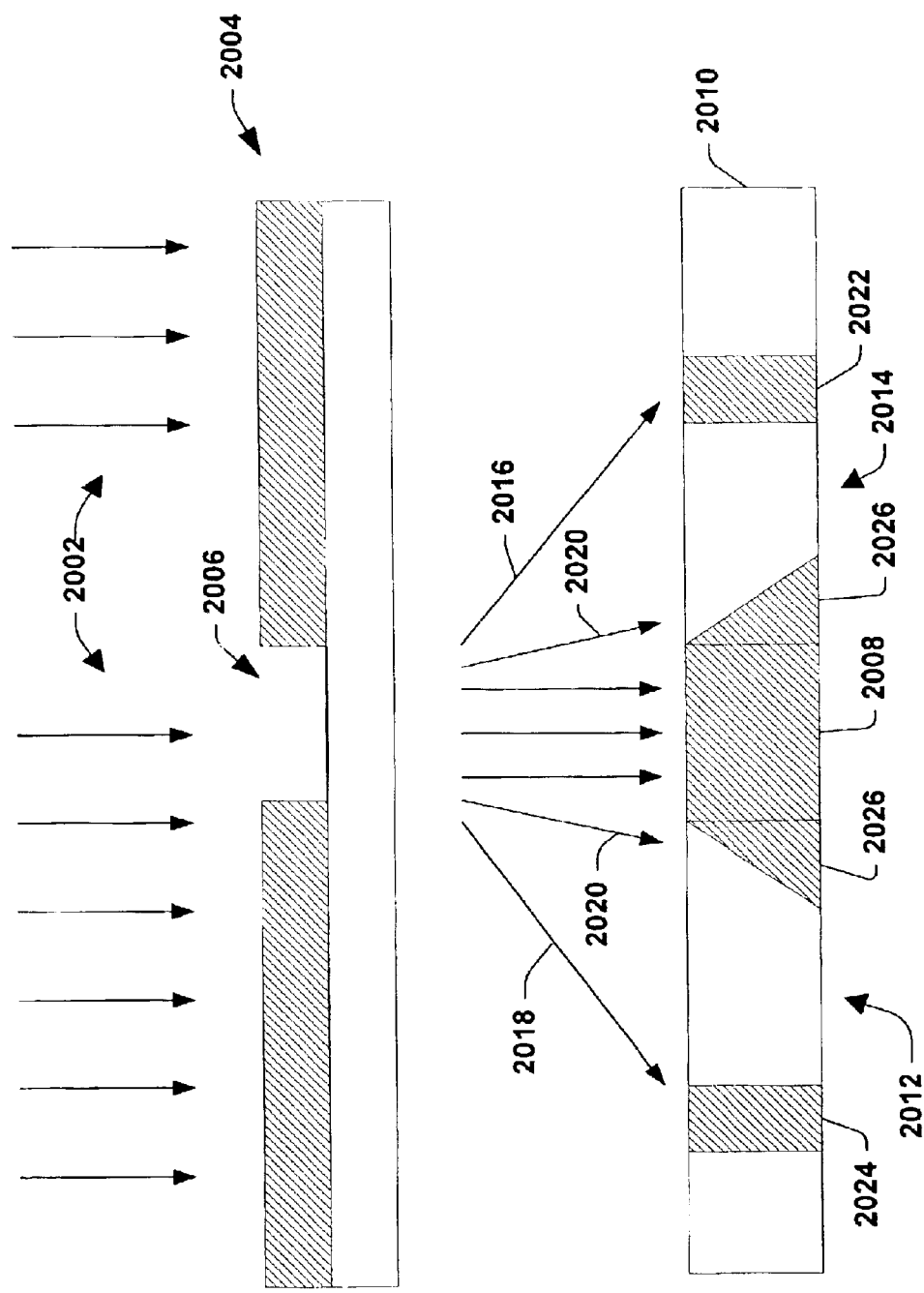
FIG. 20 illustrates conventions lithography where light waves passing through a mask or reticle are diffracted.

Turning now to FIG. 17, one of the properties from FIG. 16 is illustrated in greater detail. The substrate 1720 can be formed of one or more layers 1722, 1724 and 1726. The phase 1750 of the reflected and/or refracted light 1742 from incident light 1740 can depend, at least in part, on the thickness of a layer, for example, the layer 1724. Thus, in FIG. 18, the phase 1852 of the reflected light 1842 differs from the phase 1750 due, at least in part, to the different thickness of the layer 1824 in FIG. 18.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Using scatterometry in implementing one or more aspects of the present invention facilitates a relatively non-invasive approach to obtaining desired measurements, which can, in turn, be utilized to facilitate achieving desired results in presently occurring or subsequent processing cycles.

Although the invention has been shown and described with respect to several aspects, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means") used to describe such components are intended to correspond, unless otherwise indicated, to any item(s) which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A system that monitors and controls a phase shift mask fabrication process comprising:
    a measurement system that interacts via a beam of at least one of light and acoustic waves with features forming on at least a portion of a mask as the mask matriculates through the fabrication process; and
    a control system operatively coupled to the measurement system and one or more fabrication components to selectively adjust one or more of the fabrication components or operating parameters associated with the fabrication components to dynamically adapt the fabrication process in response to readings taken by the measurement system.

2. The system of claim 1 wherein the measurement system comprises:
    at least one of a light emitter and acoustic emitter that direct the beam incident to the mask; and
    one or more detecting components that collect portions of the beam at least one of reflected from the mask and that pass through the mask, the reflected and/or passed through beam varying in at least one of angle, intensity, phase, polarization and magnitude as the fabrication process progresses and the features evolve.

3. The system of claim 2 wherein readings taken by the measurement system are compared to at least one of predetermined data and historical test data.

4. The system of claim 3 wherein the features include at least one of defects and apertures.

5. The system of claim 4 wherein output from one or more of the detecting components can be analyzed to generate one or more signatures for comparison to one or more stored signatures to determine at least one of whether one or more defects are forming in the mask, whether one or more detects are being exaggerated as the fabrication process progresses, whether one or more defects are being formed below a surface portion of the mask, whether the apertures are being formed uniformly and whether one or more critical dimensions fall outside of acceptable tolerances.

6. The system of claim 4 wherein the defects include at least one of cracks and fractures.

7. The system of claim 6 wherein the measurement system measures at least one of depth, width and length.

8. The system of claim 1 wherein the mask includes a substantially transparent layer, through which light waves may pass, and a substantially opaque layer, through which light waves may not pass.

9. The system of claim 8 wherein the substantially transparent layer comprises quartz.

10. The system of claim 8 wherein the substantially opaque layer comprises chrome.

11. The system of claim 1 wherein the control system can selectively adjust at least one of the rate, volume and concentration of etchants applied to the mask during an etching stage.

12. The system of claim 1, employing at least one of: non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks).

13. A method for monitoring and controlling a phase shift mask fabrication process comprising:
    directing at least one of an acoustic beam and a light beam incident to the mask;
    collecting at least one of portions of the beam reflected from the mask and portions of the beam that pass through the mask; and
    determining at least one of whether one or more defects are forming in the mask, whether one or more defects are being formed below a surface portion of the mask, whether the size of a defect is increasing as the fabrication process progresses, whether one or more apertures are being formed uniformly and whether one or more critical dimensions fall outside of acceptable tolerances based on the collected light.

14. The method of claim 13 further comprising:
    detecting variations in at least one of angle, intensity, phase and polarization of at least one of the reflected beam and passed through beam as the fabrication process progresses to make one or more of the determinations.

15. The method of claim 14 further comprising:
    developing control data based upon at least one of the reflected beam and passed through beam;

feeding the control data at least one of forward and backward to one or more fabrication components; and selectively adjusting one or more of the fabrication components or one or more operating parameters associated therewith to adapt the fabrication process.

16. The method of claim 15 further comprising;

selectively adjusting at least one of the rate, volume and concentration of etchants applied to the mask during an etching stage.

17. The method of claim 13 further comprising;

focusing in on a select portion of the mask for additional monitoring if it is determined that a defect is forming in the mask.

18. The method of claim 13 further comprising:

determining whether to discard the mask or portions thereof based on a cost benefit analysis.

19. The method of claim 13 further comprising:

mapping the mask into one or more grids; and monitoring the mask at the grid mapped locations.

20. The method of claim 13 further comprising:

developing signatures from at least one of the reflected beam and passed through beam; and comparing the signatures to one or more stored signatures to make the determinations.

21. The method of claim 15 wherein the fabrication components include at least one an etching system, a projection system, a temperature system and a pressure system.

22. A system that monitors and controls a phase shift mask fabrication process comprising:

means for directing a beam of at least one of acoustic waves and light incident to features forming within at least a portion of a phase shift mask undergoing the fabrication process;

means for collecting at least one of portions of the beam reflected from the mask and portions of the beam that pass through the mask; and means for adjusting one or more fabrication components or one or more operating parameters associated with the fabrication components to adapt the fabrication process in response to the collected information.

23. The system of claim 22 further comprising:

means for analyzing the collected information to generate one or more signatures; and means for comparing the signatures to one or more stored signatures to determine at least one of whether one or more defects are forming in the mask, whether one or more defected are being formed below a surface portion of the mask, whether one or more defects are being exaggerated as the fabrication process progresses, whether the apertures are being formed uniformly and whether one or more critical dimensions fall outside of acceptable tolerances.

24. The system of claim 23 further comprising:

means for discarding the mask or a portion thereof based on cost benefit analysis.

* * * * *